(12) United States Patent
Chen et al.

(10) Patent No.: US 11,883,148 B2
(45) Date of Patent: Jan. 30, 2024

(54) SYSTEMS AND METHODS FOR MULTI-FREQUENCY COIL FOR MAGNETIC RESONANCE IMAGING

(71) Applicant: Regents of the University of Minnesota, Minneapolis, MN (US)

(72) Inventors: Wei Chen, Minneapolis, MN (US); Guangle Zhang, Minneapolis, MN (US); Wei Zhu, Minneapolis, MN (US); Xiao-Hong Zhu, Minneapolis, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 0 days.

(21) Appl. No.: 17/872,793

(22) Filed: Jul. 25, 2022

(65) Prior Publication Data

US 2023/0190129 A1    Jun. 22, 2023

Related U.S. Application Data

(60) Provisional application No. 63/225,230, filed on Jul. 23, 2021.

(51) Int. Cl.
*A61B 5/055* (2006.01)
*A61B 5/08* (2006.01)

(52) U.S. Cl.
CPC .............. *A61B 5/055* (2013.01); *A61B 5/08* (2013.01)

(58) Field of Classification Search
CPC .................................. A61B 5/055; A61B 5/08
See application file for complete search history.

(56) References Cited

U.S. PATENT DOCUMENTS

| 4,691,163 A | 9/1987 | Blass et al. |
| 4,799,016 A | 1/1989 | Rezvani |
| 2009/0118611 A1* | 5/2009 | He ..................... G01R 33/32 324/322 |

OTHER PUBLICATIONS

"A technique for double resonant operation of birdcage imaging coils", Peter M Joseph, and Dongfeng Lu, IEEE transactions for medical imaging, vol. 8, No. 3, pp. 286-294, (Year: 1989).*
"Double resonant quadrature birdcage", Jeffrey R. Fitzsimmons, Barbara L. Beck and Ralph Brooker, Mag. reson. med., vol. 30, No. 1, pp. 107-114 (Year: 1993).*

(Continued)

*Primary Examiner* — G. M. A Hyder
(74) *Attorney, Agent, or Firm* — QUARLES & BRADY LLP

(57) ABSTRACT

A system and method for performing magnetic resonance imaging (MRI), magnetic resonance spectroscopy (MRS), or magnetic resonance spectroscopy imaging (MRSI) at multiple resonant frequencies using a coil system. The coil system includes at least one conductive loop and a capacitor forming a radiofrequency (RF) resonant antenna and a tuning-matching circuit electrically connected to the RF resonant antenna to operate at multiple resonant frequencies across a desired operational range. The coil system also includes two legs electrically connecting the tuning-matching circuit to the RF resonant antenna and having a length selected to generate at least two selected resonant frequencies with a selected frequency difference.

19 Claims, 17 Drawing Sheets

(56) References Cited

OTHER PUBLICATIONS

"Microstrip RF surface coil design for extremely high-field MRI and spectroscopy", Xiaoliang Zhang, Kamil Ugurbil and Wei Chen, Mag. reson. med., vol. 46, No. 3; pp. 443-450 (Year: 2001).*

"A nested dual frequency birdcage/stripline coil for sodium/proton brain imaging at 7T", G.C. Wiggins, R. Brown, L. Fleysher, B. Zhang, B. Stoeckel, M. Inglese, and D.K. Sodickson, Proc. Intl Soc. Mag. Reson. Med. vol. 18 (Year: 2010).*

"A dual-tuned quadrature volume coil with mixed λ/2 and λ/4 microstrip resonators for multinuclear MRSI at 7T", Yong Pang, Zhentian Xie, Duan Xu, Douglas A. Kelley, Sarah J. Nelson, Daniel B. Vigneron and Xiaoliang Zhang, Mag, Reson Imaging, Feb. 2012; 30(2): 290-298 (Year: 2012).*

Ackerman et al., Mapping of Metabolites in Whole Animals by 31P NMR Using Surface Coils, Nature, 1980, 283(5743):167-170.

Alecci et al., Practical Design of a 4 Tesla Double-Tuned RF Surface Coil for Interleaved 1H and 23Na MRI of Rat Brain, Journal of Magnetic Resonance, 2006, 181(2):203-211.

Amari et al., Multiple Tuning of Birdcage Resonators, Magnetic Resonance in Medicine, 1997, 37(2):243-251.

Argov et al., Phosphorus Magnetic Resonance Spectroscopy (31P MRS) in Neuromuscular Disorders, Annals of Neurology: Official Journal of the American Neurological Association and the Child Neurology Society, 1991, 30(1):90-97.

Dabirzadeh et al., Trap Design for Insertable Second-Nuclei Radiofrequency Coils for Magnetic Resonance Imaging and Spectroscopy, Concepts in Magnetic Resonance Part B (Magnetic Resonance Engineering), 2009, 35B(3):121-132.

De Feyter et al., Deuterium Metabolic Imaging (DMI) for MRI-Based 3D Mapping of Metabolism In Vivo, Science Advances, 2018, 4(8):eaat7314, pp. 1-11.

De Graaf et al., On the Magnetic Field Dependence of Deuterium Metabolic Imaging, NMR in Biomedicine, 2020, 33(3):e4235, pp. 1-18.

Doty et al., A Multinuclear Double-Tuned Probe for Applications with Solids or Liquids Utilizing Lumped Tuning Elements, Journal of Magnetic Resonance, 1981, 43(3):399-416.

Du et al., Tightly Coupled Brain Activity and Cerebral ATP Metabolic Rate, Proceedings of the National Academy of Sciences, 2008, 105(17):6409-6414.

Fitzsimmons et al., A Transformer-Coupled Double-Resonant Probe for NMR Imaging and Spectroscopy, Magnetic Resonance in Medicine, 1987, 5(5):471-477.

Gillies et al., Applications of Magnetic Resonance in Model Systems: Tumor Biology and Physiology, Neoplasia, 2000, 2(1-2):139-151.

Hudson et al., Dual Resonant Birdcage Coils for 1H Detected 13C Microscopic Imaging at 11.7 T, Magnetic Resonance Materials in Physics, Biology and Medicine, 2000, 10:61-68.

Insko et al., Mapping of the Radiofrequency Field, Journal of Magnetic Resonance, Series A, 1993, 103(1):82-85.

Irving et al., In Vivo Determination of Body Iron Stores by Natural-Abundance Deuterium Magnetic Resonance Spectroscopy, Magnetic Resonance in Medicine, 1987, 4(1):88-92.

Isaac et al., A Design for a Double-Tuned Birdcage Coil for Use in an Integrated MRI/MRS Examination, Journal of Magnetic Resonance, 1990, 89(1):41-50.

Kan et al., A Single-Coil Triple Resonance Probe for NMR Experiments, Review of Scientific Instruments, 1980, 51(7):887-890.

Katti et al., Magnetic Resonance Imaging (MRI)—A Review, International Journal of Dental Clinics, 2011, 3(1):65-70.

Kemp et al., Absolute Quantification of Phosphorus Metabolite Concentrations in Human Muscle In Vivo by 31P MRS: A Quantitative Review, NMR in Biomedicine: An International Journal Devoted to the Development and Application of Magnetic Resonance in Vivo, 2007, 20(6):555-565.

Kendrick et al., High-Power 1H-19F Excitation in a Multiple-Resonance Single-Coil Circuit, Journal of Magnetic Resonance, 1987, 75(3):506-508.

Kreis et al., Measuring Tumor Glycolytic Flux In Vivo by Using Fast Deuterium MRI, Radiology, 2020, 294(2):289-296.

Lawry et al., Computer Modeling of Surface Coil Sensitivity, Magnetic Resonance in Medicine, 1990, 16(2):294-302.

Lei et al., In Vivo 31P Magnetic Resonance Spectroscopy of Human Brain at 7 T: An Initial Experience, Magnetic Resonance in Medicine: An Official Journal of the International Society for Magnetic Resonance in Medicine, 2003, 49(2):199-205.

Lei et al., Measurement of Unidirectional Pi to ATP Flux in Human Visual Cortex at 7 T by using In Vivo 31P Magnetic Resonance Spectroscopy, Proceedings of the National Academy of Sciences, 2003, 100(24):14409-14414.

Lu et al., In Vitro and In Vivo Studies of 17O NMR Sensitivity at 9.4 and 16.4 T, Magnetic Resonance in Medicine, 2013, 69(6):1523-1527.

Lu et al., Simultaneous Assessment of Abnormal Glycolysis and Oxidative Metabolisms in Brain Tumor using In Vivo Deuterium MRS Imaging, Proceedings of the International Society for Magnetic Resonance in Medicine (Singapore) 3962, 2016, 2 pages.

Lu et al., Quantitative Assessment of Brain Glucose Metabolic Rates using In Vivo Deuterium Magnetic Resonance Spectroscopy, Journal of Cerebral Blood Flow & Metabolism, 2017, 37(11):3518-3530.

Mateescu et al., In Vivo Assessment of Oxygen Consumption via Deuterium Magnetic Resonance, Chapter 26 of Oxygen Transport to Tissue XXXII, Springer, 2015, pp. 193-199.

Matson et al., A Practical Double-Tuned 1H/31P Quadrature Birdcage Headcoil Optimized for 31P Operation, Magnetic Resonance in Medicine: An Official Journal of the International Society for Magnetic Resonance in Medicine, 1999, 42(1):173-182.

Meyerspeer et al., An Improved Trap Design for Decoupling Multinuclear RF Coils, Magnetic Resonance in Medicine, 2014, 72(2):584-590.

Murphy-Boesch et al., Two Configurations of the Four-Ring Birdcage Coil for 1H Imaging and 1H-Decoupled 31P Spectroscopy of the Human Head, Journal of Magnetic Resonance, Series B, 1994, 103(2):103-114.

Ouwerkerk, Deuterium MR Spectroscopy: A New Way to Image Glycolytic Flux Rates, Radiology, 2020, 294(2):297-298.

Pang et al., Common-Mode Differential-Mode (CMDM) Method for Double-Nuclear MR Signal Excitation and Reception at Ultrahigh Fields, IEEE Transactions on Medical Imaging, 2011, 30(11):1965-1973.

Bresnahan Jenkins et al., Single Loop Tri-Frequency Surface Coil Design for 1H MRI and Interleaved Dynamic 2H and 17O MRS Applications at Ultrahigh Field of 16.4 T, Proceedings of the International Society for Magnetic Resonance in Medicine, 2021, 1816, 4 pages.

Qiao et al., In Vivo 31P MRS of Human Brain at High/Ultrahigh Fields: A Quantitative Comparison of NMR Detection Sensitivity and Spectral Resolution between 4 T and 7 T, Magnetic Resonance Imaging, 2006, 24(10):1281-1286.

Rajan et al., A Novel Double-Tuned Circuit for In Vivo NMR, Journal of Magnetic Resonance, 1987, 74(1):147-154.

Rath et al., Design and Performance of a Double-Tuned Bird-Cage Coil, Journal of Magnetic Resonance, 1990, 86(3):488-495.

Riis-Vestergaard et al., Glucose Metabolism in Brown Adipose Tissue Determined by Deuterium Metabolic Imaging in Rats, International Journal of Obesity, 2020, 44(6):1417-1427.

Rodgers et al., Human Cardiac 31P Magnetic Resonance Spectroscopy at 7 Tesla, Magnetic Resonance in Medicine, 2014, 72(2):304-315.

Rothman et al., 13C MRS Studies of Neuroenergetics and Neurotransmitter Cycling in Humans, NMR in Biomedicine, 2011, 24(8):943-957.

Rutledge et al., Design and Test of a Double-Nuclear RF Coil for 1H MRI and 13C MRSI at 7 T, Journal of Magnetic Resonance, 2016, 267:15-21.

Schnall et al., A New Double-Tuned Probed for Concurrent 1H and 31P NMR, Journal of Magnetic Resonance, 1985, 65(1):122-129.

Schnall et al., A Technique for Simultaneous 1H and 31P NMR at 2.2 T In Vivo, Journal of Magnetic Resonance, 1985, 63(2):401-405.

(56) References Cited

OTHER PUBLICATIONS

Shen et al., Dual-Frequency, Dual-Quadrature, Birdcage RF Coil Design with Identical B1 Pattern for Sodium and Proton Imaging of the Human Brain at 1.5 T, Magnetic Resonance in Medicine, 1997, 38(5):717-725.

Shen et al., Experimentally Verified, Theoretical Design of Dual-Tuned, Low-Pass Birdcage Radiofrequency Resonators for Magnetic Resonance Imaging and Magnetic Resonance Spectroscopy of Human Brain at 3.0 Tesla, Magnetic Resonance in Medicine: An Official Journal of the International Society for Magnetic Resonance in Medicine, 1999, 42(2):268-275.

Soares et al., Magnetic Resonance Spectroscopy of the Brain: Review of Metabolites and Clinical Applications, Clinical Radiology, 2009, 64(1):12-21.

Tomanek et al., Double-Frequency Birdcage Volume Coils for 4.7T and 7T, Concepts in Magnetic Resonance Part B (Magnetic Resonance Engineering), 2005, 26B(1):16-22.

Van De Moortele et al., B1 Destructive Interferences and Spatial Phase Patterns at 7 T with a Head Transceiver Array Coil, Magnetic Resonance in Medicine, 2005, 54(6):1503-1518.

Van De Moortele et al., Very Fast Multi Channel B1 Calibration at High Field in the Small Flip Angle Regime, Proceedings of the 17th Annual Meeting of ISMRM, 2009, 17, 1 page.

Van Der Zwaag et al., Recent Applications of UHF-MRI in the Study of Human Brain Function and Structure: A Review, NMR in Biomedicine, 2016, 29(9):1274-1288.

Van Heeswijk et al., Quantification of Brain Glycogen Concentration and Turnover through Localized 13C NMR of both the C1 and C6 Resonances, NMR in Biomedicine, 2010, 23(3):270-276.

Wang et al., A Practical Multinuclear Transceiver Volume Coil for In Vivo MRI/MRS at 7 T, Magnetic Resonance Imaging, 2012, 30(1):78-84.

Wiesner et al., Quantitative and Simultaneous Measurement of Oxygen Consumption Rates in Rat Brain and Skeletal Muscle using 17O MRS Imaging at 16.4 T, Magnetic Resonance in Medicine, 2021, 85(4):2232-2246.

Yan et al., A Hybrid Sodium/Proton Double-Resonant Transceiver Array for 9.4 T MRI, 2013 IEEE MTT-S International Microwave Workshop Series on RF and Wireless Technologies for Biomedical and Healthcare Applications (IMWS-BIO), IEEE, 2013, 3 pages.

Yan et al., A Monopole/Loop Dual-Tuned RF Coil for Ultrahigh Field MRI, Quantitative Imaging in Medicine and Surgery, 2014, 4(4):225-231.

Yang et al., Analysis of Wave Behavior in Lossy Dielectric Samples at High Field, Magnetic Resonance in Medicine: An Official Journal of the International Society for Magnetic Resonance in Medicine, 2002, 47(5):982-989.

Zhang et al., A Dual-Frequency Surface Coil Design Comprised of a Single Loop for Both Proton and Deuterium Magnetic Resonance Imaging at 16.4 T, Proceedings of the 28th Annual Meeting of ISMRM, Virtual Conference, 2020, 4105, 3 pages.

Zhu et al., 17O Relaxation Time and NMR Sensitivity of Cerebral Water and their Field Dependence, Magnetic Resonance in Medicine: An Official Journal of the International Society for Magnetic Resonance in Medicine, 2001, 45(4):543-549.

Zhu et al., In Vivo 17O NMR Approaches for Brain Study at High Field, NMR in Biomedicine: An International Journal Devoted to the Development and Application of Magnetic Resonance In Vivo, 2005, 18(2):83-103.

Zhu et al., Quantitative Imaging of Energy Expenditure in Human Brain, Neuroimage, 2012, 60(4):2107-2117.

Zhu et al., In Vivo 17O MRS Imaging-Quantitative Assessment of Regional Oxygen Consumption and Perfusion Rates in Living Brain, Analytical Biochemistry, 2017, 529:171-178.

Zhu et al., In Vivo X-Nuclear MRS Imaging Methods for Quantitative Assessment of Neuroenergetic Biomarkers in Studying Brain Function and Aging, Frontiers in Aging Neuroscience, 2018, 10(394):1-16.

Zhu et al., Quantitative imaging of Brain Energy Metabolisms and Neuroenergetics using In Vivo X-Nuclear 2H, 17O and 31P MRS at Ultra-High Field, Journal of Magnetic Resonance, 2018, 292:155-170.

* cited by examiner

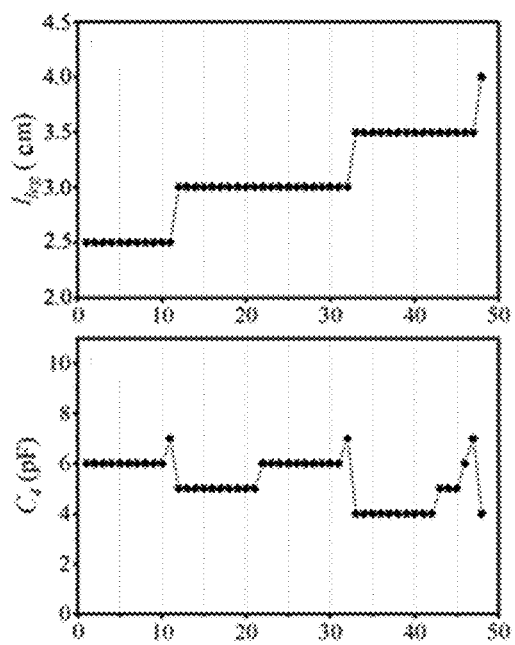
FIG. 4A
FIG. 4B
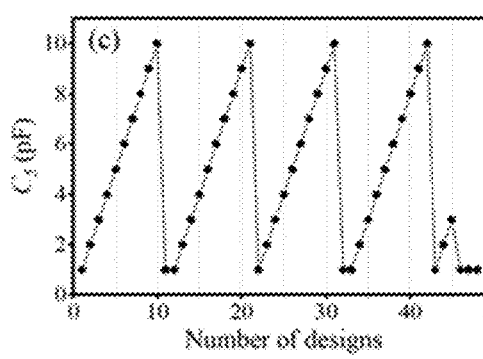
FIG. 4C
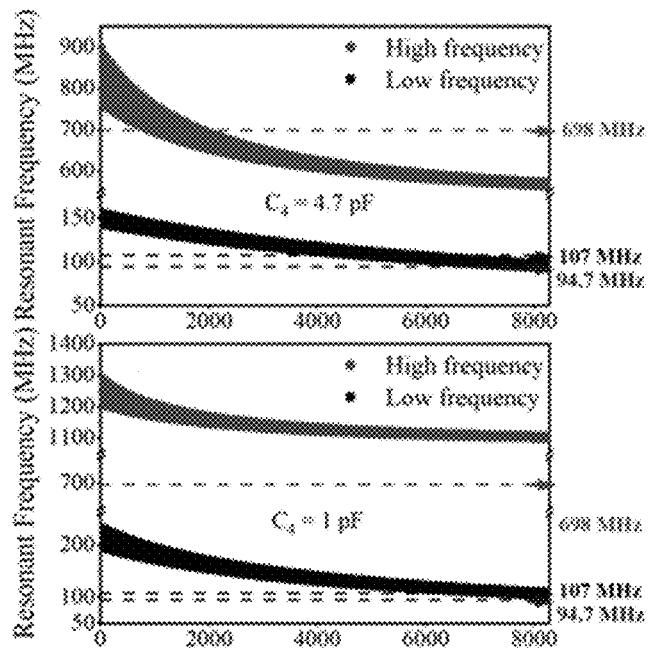
FIG. 4D
FIG. 4E
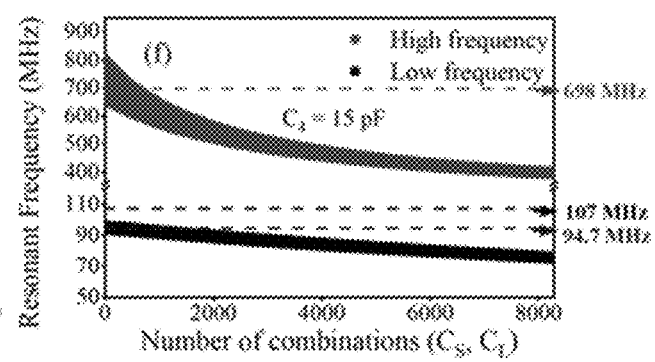
FIG. 4F FIG. 6A
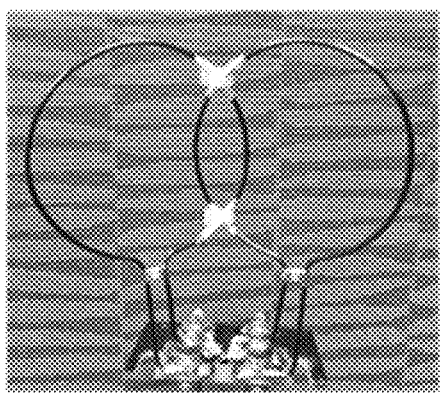
FIG. 6B
| Resonant Frequency (MHz) | 107 ($^2$H) | 698 ($^1$H) |
|---|---|---|
| $S_{11}$ (dB) (Channel 1) | -25 | -36 |
| $S_{22}$ (dB) (Channel 2) | -26 | -44 |
| $S_{21}$ (dB) | -15 | -46 |
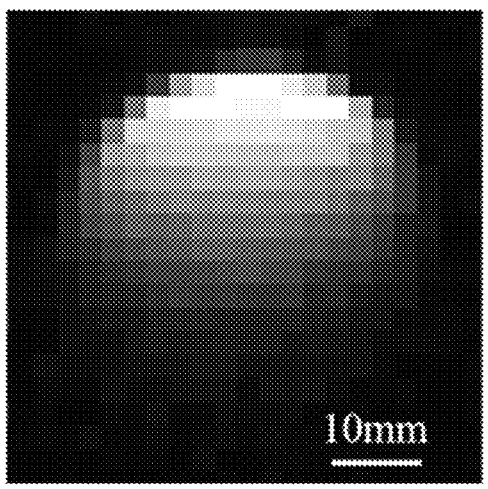
FIG. 6C
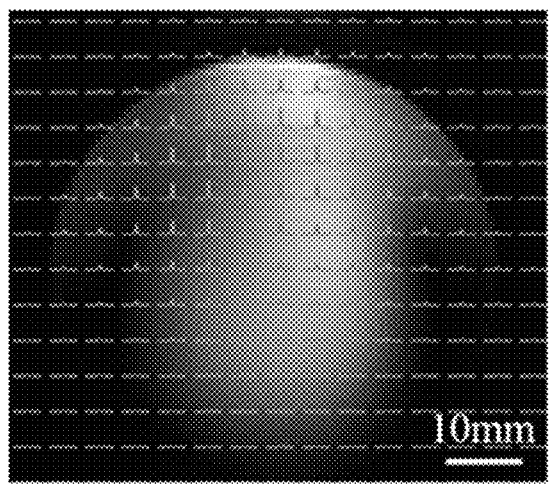
FIG. 6D

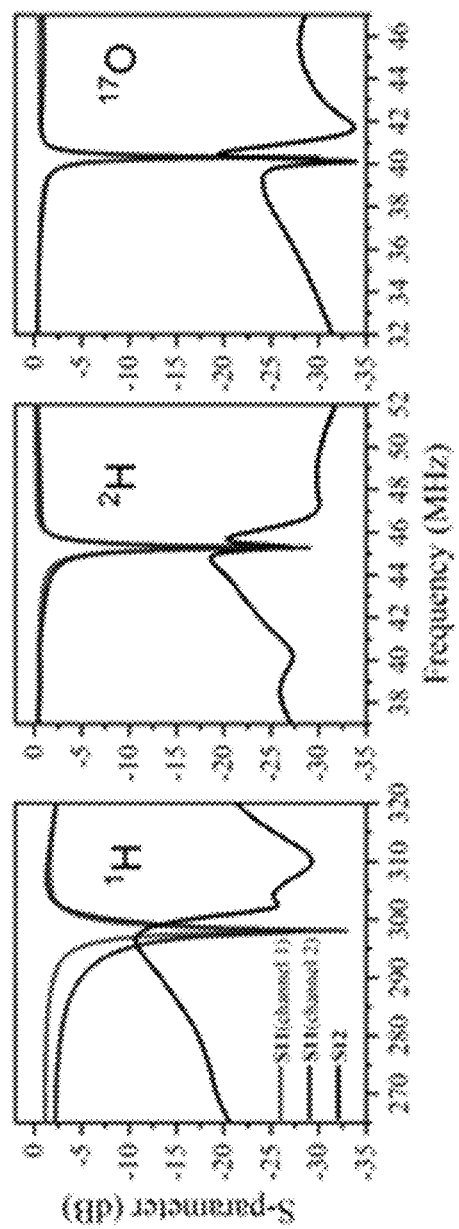
FIG. 10A
FIG. 10B
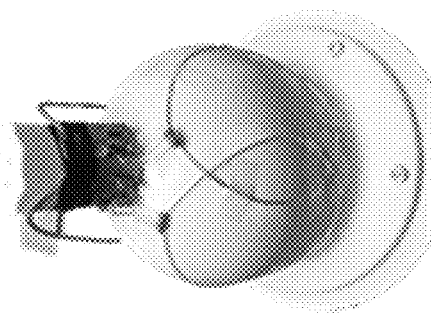
FIG. 10C
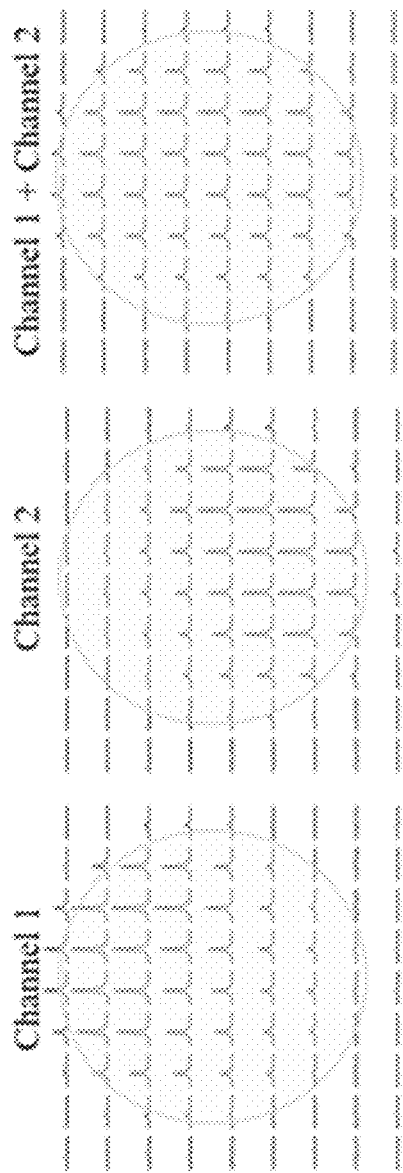
FIG. 10D

SYSTEMS AND METHODS FOR MULTI-FREQUENCY COIL FOR MAGNETIC RESONANCE IMAGING

CROSS REFERENCE TO RELATED APPLICATIONS

The present application is based on, claims priority to, and incorporates herein by reference for all purposes, U.S. Provisional Application Ser. No. 63/225,230, filed Jul. 23, 2021.

STATEMENT REGARDING FEDERALLY-SPONSORED RESEARCH

This invention was made with government support under MH111413, CA240953, EB027061, and EB026978 awarded by National Institutes of Health. The government has certain rights in the invention.

BACKGROUND

The present disclosure relates to systems and methods for magnetic resonance imaging (MRI) and/or magnetic resonance spectroscopy (MRS), and/or magnetic resonance spectroscopic imaging (MRSI). More particularly, the present disclosure relates to systems and methods for radiofrequency (RF) coils for use in MRI, MRS, and MRSI systems.

When a substance such as human tissue is subjected to a uniform magnetic field (polarizing field $B_0$), the individual magnetic moments of the nuclear spins in the tissue attempt to align with this polarizing field, but precession about it in random order at their characteristic Larmor frequency. Usually the nuclear spins are comprised of hydrogen atoms, but other nuclear magnetic resonance (NMR) active nuclei are also used, as will be described. A net magnetic moment (Mz) is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$; also referred to as the radiofrequency (RF) field) which is in the x-y plane and is near the Larmor frequency, the net aligned moment, Mz, may be rotated, or "tipped" into the x-y plane to produce a net transverse magnetic moment Mt, which is rotating, or spinning, in the x-y plane at the Larmor frequency. The practical value of this phenomenon resides in the signal which is emitted by the excited spins after the excitation field $B_1$ is terminated. There are a wide variety of measurement sequences in which this NMR phenomenon is exploited.

When utilizing these signals to produce images, magnetic field gradients in three perpendicular directions (Gx, Gy, and Gz) are employed. Typically, the region to be imaged experiences a sequence of measurement cycles in which these gradients vary according to the particular localization (or imaging) method being used. The emitted MR signals are detected using a RF receiver coil.

MRI, MRS, and MRSI are versatile tools for in vivo studies of human health and diagnosis of diseases. Although most MRI and MRS studies are based on proton-1 ($^1$H) detection, other non-proton or X-nuclear MRS studies provide essential information that cannot be obtained by $^1$H MRI or MRS. For example, carbon-13 ($^{13}$C) MRS has been used for decades for the assessment of neurotransmission cycling activity and cell-specific neuroenergetics to help uncover the physiopathological mechanisms underlying neurological and psychiatric diseases. Phosphorus-31 ($^{31}$P) MRS has been an invaluable approach for studying high-energy phosphate metabolism in the cardiac or skeletal muscles, the brain, and other organs in vivo or tissues in situ. Oxygen-17 ($^{17}$O) MRS or MRI, which has a relatively short history, has the potential to become a valuable MR imaging tool for quantifying mitochondrial respiration rate and improving our understanding of the mechanisms underlying metabolic dysfunction in diseased states. Furthermore, deuterium ($^2$H) MRS, owing to its versatility, robustness, and ease of implementation, has recently attracted much interest because it provides a unique and robust imaging tool capable of simultaneously assessing glycolysis and tricarboxylic acid (TCA) cycle activities in the brains and other organs of humans and animals. The $^2$H MRSI has shown promise for brain tumor imaging and a potential for clinical diagnosis.

Although X-nuclear MRI/MRS/MRSI measurements acquire valuable information associated with the X-nuclei of interest, they still require proton detection for $B_0$ shimming and structural (anatomic) or functional imaging. Therefore, a dual-frequency coil at RF regime, which can be electronically tuned and matched at both proton and X-nuclear frequencies, is desired. A variety of multi-frequency RF coil designs have been attempted. For example, Kan et al. reported the first single-coil triple-resonance probe, which was based on fundamental circuit theory, for $^1$H-$^2$H-$^{13}$C NMR experiments in 1980, as described in Kan S, Fan M, Courtieu J. A. Review of Scientific Instruments 1980; 51(7): 887-890. Some have made switching circuits in different applications, such as described in Mispelter J, Lupu M, Briguet A. NMR probeheads for biophysical and biomedical experiments: theoretical principles & practical guidelines: Imperial College Press; 2006.

Using a similar circuit concept, several other surface coils have been designed and reported. In 1989, Joseph et al. built a "birdcage" volume coil to generate homogeneous RF magnetic fields at two desired resonant frequencies for multinuclear NMR imaging, which is described in Joseph P M, Lu D. A technique for double resonant operation of birdcage imaging coils. IEEE transactions on medical imaging 1989; 8(3):286-294.

Various double-tuned birdcage imaging coils have also been designed. Among them, a quadrature double-tuned birdcage coil was developed to enable the application of birdcage coils in X-nuclear MRSI, as described in Fitzsimmons J R, Beck B L, Ralph Brooker H. Double resonant quadrature birdcage. Magnetic resonance in medicine 1993; 30(1):107-114.

With the rapid development and utilization of high/ultra-high magnetic field scanners in research and clinical applications, it became challenging to reach very-high $^1$H operation frequencies at ultrahigh fields (UHF) using the traditional birdcage design. Zhang et al. subsequently introduced a novel RF surface coil design based on the microstrip transmission line concept for UHF MRI and MRSI applications, as described in Zhang X, Ugurbil K, Chen W. Microstrip R F surface coil design for extremely high-field MRI and spectroscopy. Magnetic Resonance in Medicine 2001; 46(3):443-450. The microstrip design was later combined with the birdcage design (Wiggins G, Brown R, Fleysher L, Zhang B, Stoeckel B, Inglese M, Sodickson D. A nested dual frequency birdcage/stripline coil for sodium/proton brain imaging at 7T. 2010. ISMRM. p 2159.), quadrature design (Pang Y, Xie Z, Xu D, Kelley D A, Nelson S J, Vigneron D B, Zhang X. A dual-tuned quadrature volume coil with mixed λ/2 and λ/4 microstrip resonators for multinuclear MRSI at 7T. Magnetic resonance imaging 2012; 30(2):290-298.), and loop design (Yan X, Shi L, Wei L, Zhuo Y, Zhou X J, Xue R. A hybrid sodium/proton double-resonant transceiver array for 9.4T MRI. 2013. IEEE. p 1-3.) to create dual-frequency coils for UHF MRI and spectroscopy applications.

Conventional dual-frequency surface coil designs usually consist of two separated RF coils (one for $^1$H and the other for X-nucleus). Electromagnetic (EM) coupling between the X-nucleus and proton coil channels may reduce the coil factor (Q), leading to degraded proton and X-nuclear signal detection sensitivities, thus, performance.

Many researchers have proposed improved designs to solve the coupling problem at higher frequencies (Fitzsimmons J R, Beck B L, Ralph Brooker H. Double resonant quadrature birdcage. Magnetic resonance in medicine 1993; 30(1):107-114.; Amari S, Müfit Uluğ A, Bornemann J, Van Zijl P C, Barker P B. Multiple tuning of birdcage resonators. Magnetic resonance in medicine 1997; 37(2):243-251.; Pang Y, Xie Z, Xu D, Kelley D A, Nelson S J, Vigneron D B, Zhang X. A dual-tuned quadrature volume coil with mixed λ/2 and λ/4 microstrip resonators for multinuclear MRSI at 7T. Magnetic resonance imaging 2012; 30(2):290-298.; Pang Y, Zhang X, Xie Z, Wang C, Vigneron D B. Common-mode differential-mode (CMDM) method for double-nuclear MR signal excitation and reception at ultrahigh fields. IEEE transactions on medical imaging 2011; 30(11): 1965-1973.; and Wang C, Li Y, Wu B, Xu D, Nelson S J, Vigneron D B, Zhang X. A practical multinuclear transceiver volume coil for in vivo MRI/MRS at 7T. Magnetic resonance imaging 2012; 30(1):78-84.). For example, trap circuits have been introduced into the X-nuclear coil to block the current induced at the proton frequency while the coil resonates at a lower X-nuclear frequency (Dabirzadeh A, McDougall MP. Trap design for insertable second-nuclei radiofrequency coils for magnetic resonance imaging and spectroscopy. Concepts in Magnetic Resonance Part B: Magnetic Resonance Engineering: An Educational Journal 2009; 35(3):121-132.; Alecci M, Romanzetti S, Kaffanke J, Celik A, Wegener H, Shah N. Practical design of a 4 Tesla double-tuned RF surface coil for interleaved $^1$H and $^{23}$Na MRI of rat brain. Journal of Magnetic Resonance 2006; 181(2):203-211.; and Meyerspeer M, Roig E S, Gruetter R, Magill A W. An improved trap design for decoupling multinuclear RF coils. Magnetic resonance in medicine 2014; 72(2):584-590.).

The $^1$H and X-nuclear RF coils have also been arranged so that they partially overlap in space to cancel the mutually induced RF currents, thereby achieving intrinsic EM decoupling, such as described in Yan X, Xue R, Zhang X. A monopole/loop dual-tuned RF coil for ultrahigh field MRI. Quantitative imaging in medicine and surgery 2014; 4(4): 225. and Rutledge 0, Kwak T, Cao P, Zhang X. Design and test of a double-nuclear RF coil for $^1$H MRI and $^{13}$C MRSI at 7T. Journal of Magnetic Resonance 2016; 267:15-21. Nevertheless, such coupling problems make it difficult to design a dual-frequency multi-coil array that can offer a better detection sensitivity than the birdcage volume coil. Moreover, these simple single-loop surface coils are not able to achieve a high $^1$H resonant frequency at UHF. For instance, the highest resonant frequency that can be achieved is only 394 MHz when 16-AWG copper wire is used to construct a 5 cm-diameter single-loop coil with a (single) variable tuning capacitor (usually with a minimum value of 1 pF). This frequency is far below the $^1$H resonant (or Larmor) frequency of 698 MHz at 16.4T, although the same coil can be readily tuned to X-nuclei resonant frequencies. The maximum coil diameter that can reach 698 MHz (without using the slip or distributed capacitor(s)) is 1.9 cm. Similarly, the maximum coil diameter for $^1$H at 7T is 7.7 cm, which might be too small for human brain or body $^1$H imaging applications.

Thus, there is a need for systems and methods that provide robust designs of RF coil(s) that can operate at $^1$H and X-nuclear frequencies, including for operation at lower resonant frequencies, for instance, for $^2$H or $^{17}$O MRSI in which the Larmor frequency is 6-7 times lower than that of $^1$H.

SUMMARY

The present disclosure overcomes the aforementioned drawbacks by providing systems and methods for multi-frequency resonant coils or coil arrays with intrinsic decoupling and the ability to operate at multiple resonant frequencies of interest with an optimal performance for the X-nuclear resonant frequencies. In one non-limiting example, a multi-frequency resonant surface or array coil is provided that includes an LC circuit design enabling broad X-nuclear MRS, MRSI or MRI applications, including at high or ultrahigh fields.

In accordance with one aspect of the disclosure, a radiofrequency (RF) coil system is provided for performing magnetic resonance imaging (MRI), magnetic resonance spectroscopy (MRS), or magnetic resonance spectroscopy imaging (MRSI) at multiple resonant frequencies. The coil system includes at least one conductive loop and a capacitor forming an RF resonant antenna and a tuning-matching circuit electrically connected to the RF resonant antenna to generate multiple resonant frequencies across a desired operational range. The coil system also includes two conductive legs electrically connecting the tuning-matching circuit to the RF resonant antenna and having a length selected to generate at least two selected resonant frequencies with a selected frequency difference.

In accordance with another aspect of the disclosure, a method is provided for designing a coil system for performing magnetic resonance imaging (MRI), magnetic resonance spectroscopy (MRS) or magnetic resonance spectroscopy imaging (MRSI) operated at multiple resonant frequencies. The method. includes selecting at least one conductive loop and at least one capacitor to form a radiofrequency (RF) resonant antenna and configuring a tuning-matching circuit electrically connected to the RF resonant antenna to generate multiple resonant frequencies across a desired operational range. The method further includes electrically connecting two conductive legs between the tuning-matching circuit and the capacitor of the RF resonant antenna and selecting components of the tuning-matching circuit and parameters of the conductive loop and the two legs to have a quantitative relationship between all capacitances and inductances under unloaded conditions, where the induced reactance is zero, using a modeled relationship. In one, non-limiting example, the modeled relationship may include $$\frac{1}{\frac{1}{\frac{1}{\frac{1}{\omega_0 L_2}-\omega_0 C_4}+\omega_0 L_1}-\omega_0 C_L}-\frac{1}{\omega_0 C_5}-\frac{1}{\omega_0 C_S}=0,$$

wherein $\omega_0$ represents each of the multiple resonant frequencies of the coil, $C_S$ is a matching capacitor, $C_L$ is a tuning capacitor, Li is inductance of the two legs, $L_2$ is inductance of the conductive loop, and $C_4$ is a fixed capacitance of the tuning-matching circuit.

The foregoing and other aspects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 4A is a graph of varied $l_{leg}$ (total wire leg length) values for the qualified designs with a tolerance (prcnt) of 20%, which are obtained based on $d_{wire}$ (coil loop wire diameter)=1.29 mm, $l_{loop}$ (coil loop perimeter)=5.0×π=15.7 cm, 1 pF≥$C_S$≤23 pF, 1 pF≤$C_L$≤23 pF, $l_{leg}$=[2.0, 2.5, 3.0, 3.5, 4.0, 4.5] cm, and $C_4$, $C_5$=1:1:10 pF through calculation following the process of FIG. 3.

FIG. 4B is a graph of varied $C_4$ values for the qualified designs with a tolerance (prcnt) of 20%, which are obtained based on $d_{wire}$=1.29 mm, $l_{loop}$=5.0×π=15.7 cm, 1 pF≤$C_S$≤23 pF, 1 pF≤$C_L$≤23 pF, $l_{leg}$=[2.0, 2.5, 3.0, 3.5, 4.0, 4.5] cm, and $C_4$, $C_5$=1:1:10 pF through calculation following the process of FIG. 3.

FIG. 4C is a graph of varied $C_S$ values for the qualified designs with a tolerance (prcnt) of 20%, which are obtained based on $d_{wire}$=1.29 mm, $l_{loop}$=5.0×π=15.7 cm, 1 pF≤$C_S$≤23 pF, 1 pF≤$C_L$≤23 pF, $l_{leg}$=[2.0, 2.5, 3.0, 3.5, 4.0, 4.5] cm, and $C_4$, $C_5$=1:1:10 pF through calculation following the process of FIG. 3.

FIG. 4D is a graph of simulated resonant frequency ranges of the dual-frequency resonant surface coil (Larmor frequency at 16.4T: 698 MHZ for $^1H$; 107 MHz for $^2H$ and 94.7 MHz for 170) of FIG. 2A with 5-cm loop diameter obtained with $d_{wire}$=1.29 mm, $l_{loop}$=5.0×π cm, $l_{leg}$=3.5 cm, $C_4$=4.7 pF, $C_5$=2.2 pF, and ($C_S$, $C_L$)=1:0.1: 10 pF.

FIG. 4E is a graph of simulated resonance frequency ranges obtained with the same values used for FIG. 4D, but with a $C_4$ value of 1 pF.

FIG. 4F is a graph of simulated resonance frequency ranges obtained with the values used for FIG. 4D, but with a $C_4$ value of 15 pF.

FIG. 6A is an image of a prototype quadrature coil array comprised of two identical $^1H$-$^2H$ dual-frequency surface loop coils (5 cm diameter).

FIG. 6B is a table of S parameters ($S_{11}$, $S_{22}$ and $S_{21}$) of two channels in the $^1H$-$^2H$ dual-frequency quadrature coil array of FIG. 6A.

FIG. 6C is a representative sagittal $^2H$ GEMS (gradient-echo multi-slice) image of a phantom cropped acquired using the $^1H$-$^2H$ dual-frequency quadrature coil array of FIG. 6A to show only the imaging area with significant $^2H$ water signals.

FIG. 6D is a representative axial $^2H$ CSI (chemical shift image) of a water phantom overlaid on the corresponding proton image (only areas with significant $^2H$ signals are displayed) acquired using the $^1H$-$^2H$ dual-frequency quadrature coil array of FIG. 6A.

FIG. 7B is a set of graphics showing experimental results: coronal $B_1$ maps (top) and central normalized $B_1$ profiles (bottom), between the traditional $^1H$ single frequency coil (FIG. 2D) and the dual-frequency coil (FIG. 2A) operating at $^1H$ frequency at 16.4T. Both simulation (FIG. 7A) and experimental (FIG. 7B) results show that the $^1H$ $B_1$ strength reduced about half for the dual-frequency coil, however, the $B_1$ distributions for both coils are similar.

FIG. 10A is an image of a human head size transreceiver coil array (two channels) with the triple resonant frequency ($^1$H-$^{17}$O-$^2$H) tuning ability for 7T human imaging applications.

FIG. 10B is a set of correlated graphs showing S11 and S12 measurements of both array channels (FIG. 10A) obtained using a Network Analyzer under coil loaded condition with a 15 cm-diameter sphere containing 50 mM NaCl solution.

FIG. 10C is an example proton image of water phantom acquired using the coil of FIG. 10A.

FIG. 10D is a set of representative $^{17}$O CSIs acquired using the coil of FIG. 10A.

DETAILED DESCRIPTION

Figure 1:
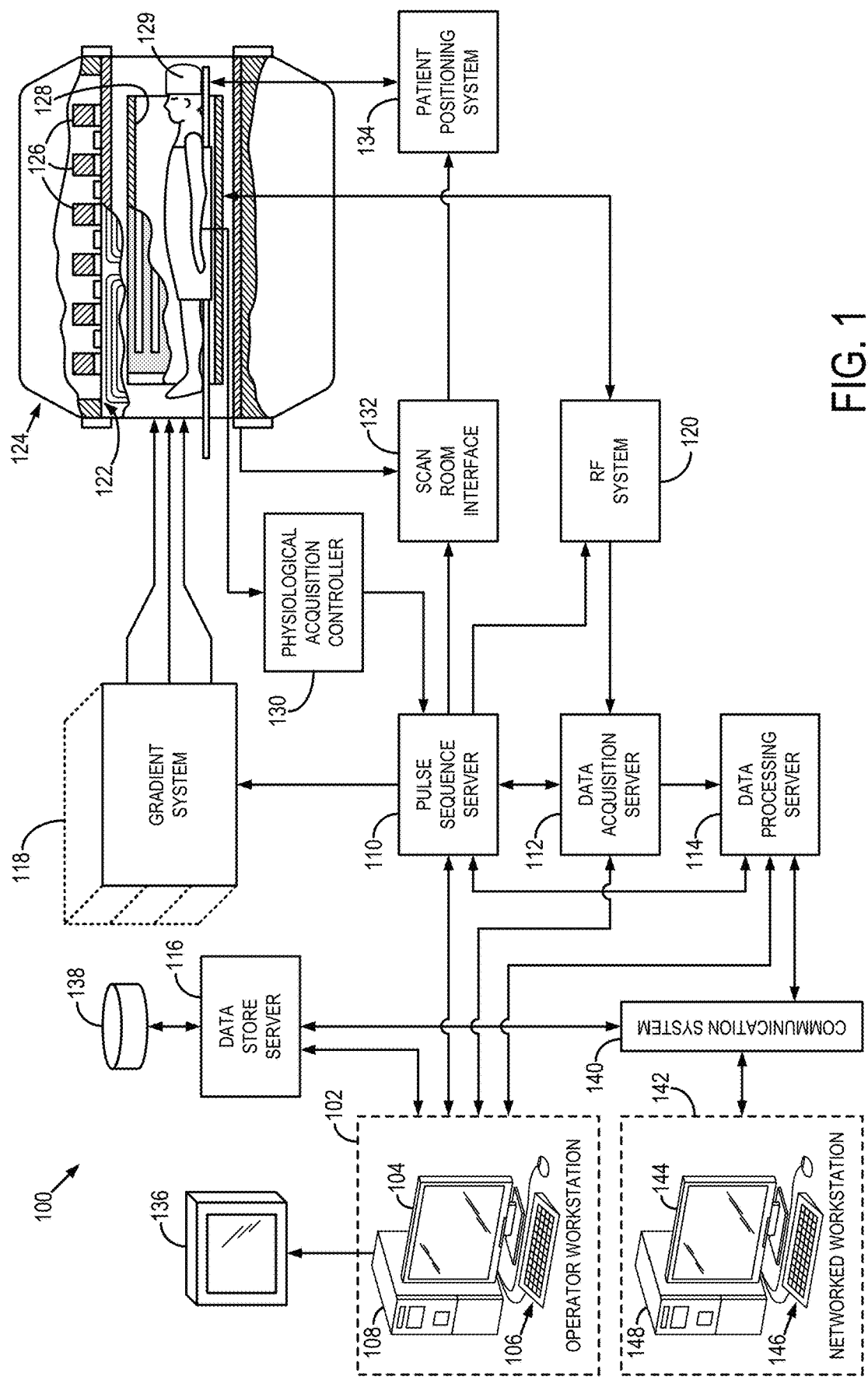
FIG. 1 is a schematic block diagram of a magnetic resonance imaging system configured for use in accordance with the systems and methods described herein.

Referring particularly to FIG. 1, one non-limiting example of a system 100 for magnetic resonance (MR) imaging (MRI), magnetic resonance spectroscopy (MRS), and/or magnetic resonance spectroscopic imaging (MRSI) is illustrated. The system 100 includes a workstation 102 having a display 104 and a keyboard 106. The workstation 102 includes a processor 108 that is commercially available to run a commercially-available operating system. The workstation 102 provides the operator interface that enables scan prescriptions to be entered into the MRI system 100. The workstation 102 may be connected to four servers: a pulse sequence server 110; a data acquisition server 112; a data processing server 114; and a data store server 116. These servers may be virtual or physical. The workstation 102 and each server 110, 112, 114, and 116 are connected to communicate with each other.

The pulse sequence server 110 functions in response to instructions downloaded from the workstation 102 to operate a gradient system 118 and a radiofrequency (RF) system 120. Gradient waveforms necessary to perform the prescribed scan are produced and applied to the gradient system 118, which controls gradient coils in an assembly 122 to produce the magnetic field gradients Gx, Gy, and Gz used for position encoding MR signals, thus, generating MR imaging. The gradient coil assembly 122 forms part of a magnet assembly 124 that includes a polarizing magnet 126 and a whole-body RF coil 128 and/or a local RF coil 129.

As will be described, the RF coil 128/129 may be a single coil or a coil array, which can operate for RF transmission (transmitter coil), RF reception (receiver coil) or for both RF transmission and reception (transreceiver coil). More particularly, the RF coil 128/129 may be a multi-frequency resonant coil or coil array, as will be described. In one non-limiting example that will be described, the RF coil 128/129 can include an RF antenna, for example, such as a loop resonator coil. In one example, an LC resonant loop and a tuning-matching circuit is bridged by two short wires (or coil legs) with the desired lengths to generate two resonant frequencies for the same resonant coil with a very large frequency difference. This and the other designs described herein may be realized in a variety of different configurations.

RF excitation waveforms are applied to the RF coil 128/129, or a separate local coil, such as a head coil, by the RF system 120 to perform the prescribed magnetic resonance pulse sequence. Responsive MR signals detected by the RF coil 128/129, or a separate local coil, are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128/129 or to one or more local coils or coil arrays.

The RF system 120 also includes one or more RF receiver channels. Each RF receiver channel includes an RF preamplifier that amplifies the MR signal received by the coil 128/129 to which it is connected, and a detector that detects and digitizes the quadrature components of the received MR signal, resulting in complex free induction decay (FID) data. The Fourier transformation (FT) of the FID generates a spectrum with phase and resonance signal information. The magnitude of the received MR signal may thus be determined at any sampled point by the square root of the sum of the squares of the I and Q components:

$$M = \sqrt{I^2 + Q^2} \qquad \text{Eqn. 1;}$$

and the phase of the received MR signal may also be determined:

$$\varphi = \tan^{-1}\left(\frac{Q}{I}\right). \qquad \text{Eqn. 2}$$

The pulse sequence server 110 also optionally receives patient data from a physiological acquisition controller 130. The controller 130 receives signals from a number of different sensors connected to the patient, such as electrocardiograph (ECG) signals from electrodes, or respiratory signals from a bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. In all these examples, the data acquisition server 112 acquires MR data and processes it in real-time to produce information that is used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a back projection image reconstruction of acquired MR data; the generation of functional MR images or MRSI (e.g., acquired using the chemical shift imaging method); and the calculation of motion or flow images.

Images reconstructed by the data processing server 114 are conveyed back to the workstation 102 where they are stored. Images may be displayed on the operator display 104 or a display 136 that is located near the magnet assembly 124 for use by attending physicians or other clinicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network or communication system 140 to other facilities that may include other networked workstations 142.

The communication system 140 and networked workstation 142 may represent any of the variety of local and remote computer systems that may be included within a given clinical or research facility including the system 100 or other, remote location that can communicate with the system 100. In this regard, the networked workstation 142 may be functionally and capably similar or equivalent to the operator workstation 102, despite being located remotely and communicating over the communication system 140. As such, the networked workstation 142 may have a display 144 and a keyboard 146. The networked workstation 142 includes a processor 148 that is commercially available to run a commercially-available operating system. The networked workstation 142 may be able to provide the operator interface that enables scan prescriptions to be entered into the MRI system 100.

Multi-Frequency Coil Design

The multi-frequency loop coil or array design of the present disclosure can utilize a new RF coil circuit and/or a switching design. As will be described herein, the following denotations will be used:

$B_0$: static magnetic field strength (Tesla or T)
$f_{proton}$: proton's Larmor frequency at $B_0$ (MHz)
$f_{(x-nuclei)}$: X-nuclei's Larmor frequency at $B_0$ (MHz)
prcnt: tuning tolerance (percentage)
$l_{loop}$: coil-loop perimeter (mm)
$d_{wire}$: coil copper (or silver) wire diameter (mm)
$l_{leg}$: coil-leg total length (mm)
$C_S$: matching capacitance $C_S$
$C_L$: tuning capacitance $C_L$
$C_5$: balanced matching capacitance (close to $C_S$)
$L_1$: inductance from the coil legs
$L_2$: inductance from the coil loop
$R_{(f0,high)}$: high-frequency limit (MHz)
$R_{(f0,low)}$: low-frequency limit (MHz).

Figure 2A:
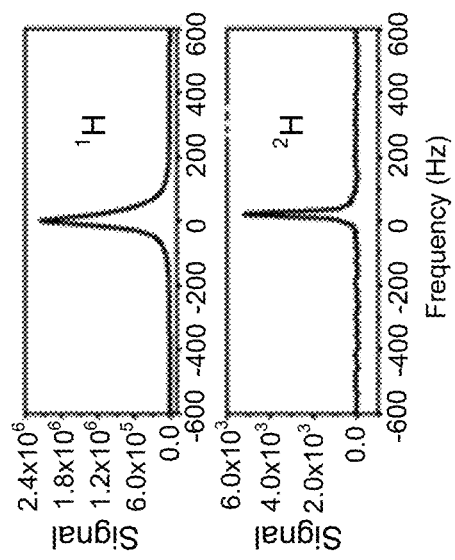
FIG. 2A is an image of prototype $^1H$-$^2H$ dual-frequency single-loop surface coil (without split capacitors) for 16.4T imaging applications in accordance with the present disclosure.
Figure 2B:
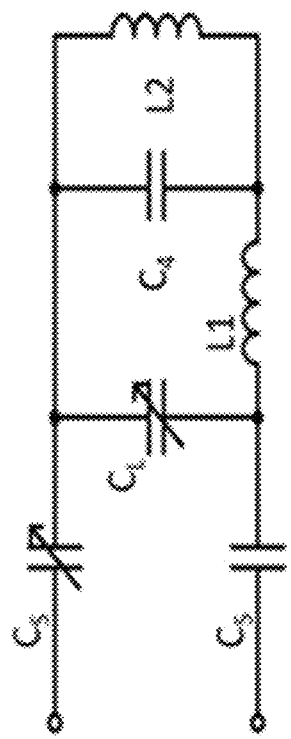
FIG. 2B is a circuit diagram of prototype $^1H$-$^2H$ dual-frequency coil of FIG. 2A.
Figure 2C:
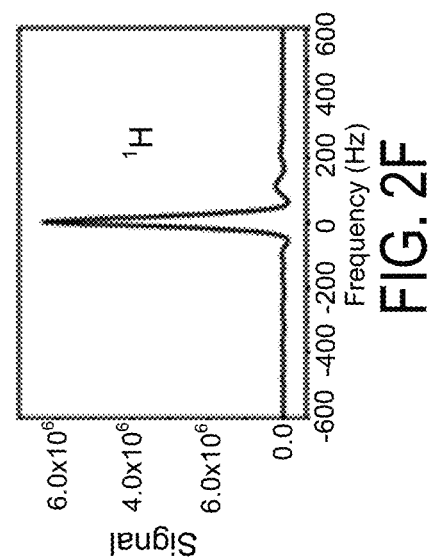
FIG. 2C is a set of correlated graphs showing the global $^1H$ and $^2H$ free induction decay (FID) signals acquired using the $^1H$-$^2H$ dual-frequency coil of FIG. 2A.

Referring to FIG. 2A, in one non-limiting example, a dual-frequency, $^1$H-$^2$H RF coil is shown. In this non-limiting example, the RF antenna is formed by a single-loop surface coil for 16.4T imaging applications. The coil was designed to include an LC ($L_2$ and $C_4$) resonant circuit design. The coil of FIG. 2A includes of four capacitors ($C_S$, $C_L$, $C_4$, and $C_5$) and an open-loop (5 cm in diameter) made of enameled copper wire (16 AWG: wire diameter of 1.29 mm). The corresponding circuit diagram is shown in FIG. 2B. To generate multiple resonances in the coil, the reactance is eliminated to make the circuit a purely resistive element, so that the current in the coil and, therefore, the RF magnetic field ($B_1$) generated by the coil, are maximized, and its performance as a resonant coil is optimized. Equation 3 describes the quantitative relationship between all the capacitances and inductances, and the resonant (or Larmor) frequencies (o) of the coil (as depicted in FIG. 2B) under unloaded conditions, where the induced reactance is zero.

$$\cfrac{1}{\cfrac{1}{\cfrac{1}{\cfrac{1}{\omega_0 L_2} - \omega_0 C_4} + \omega_0 L_1} - \omega_0 C_L} - \cfrac{1}{\omega_0 C_5} - \cfrac{1}{\omega_0 C_S} = 0. \qquad \text{Eqn. 3}$$

Using a design process in accordance with the present disclosure allows one to select appropriate capacitance and inductance values for given resonant frequencies based on Eqn. 3.

Figure 3:
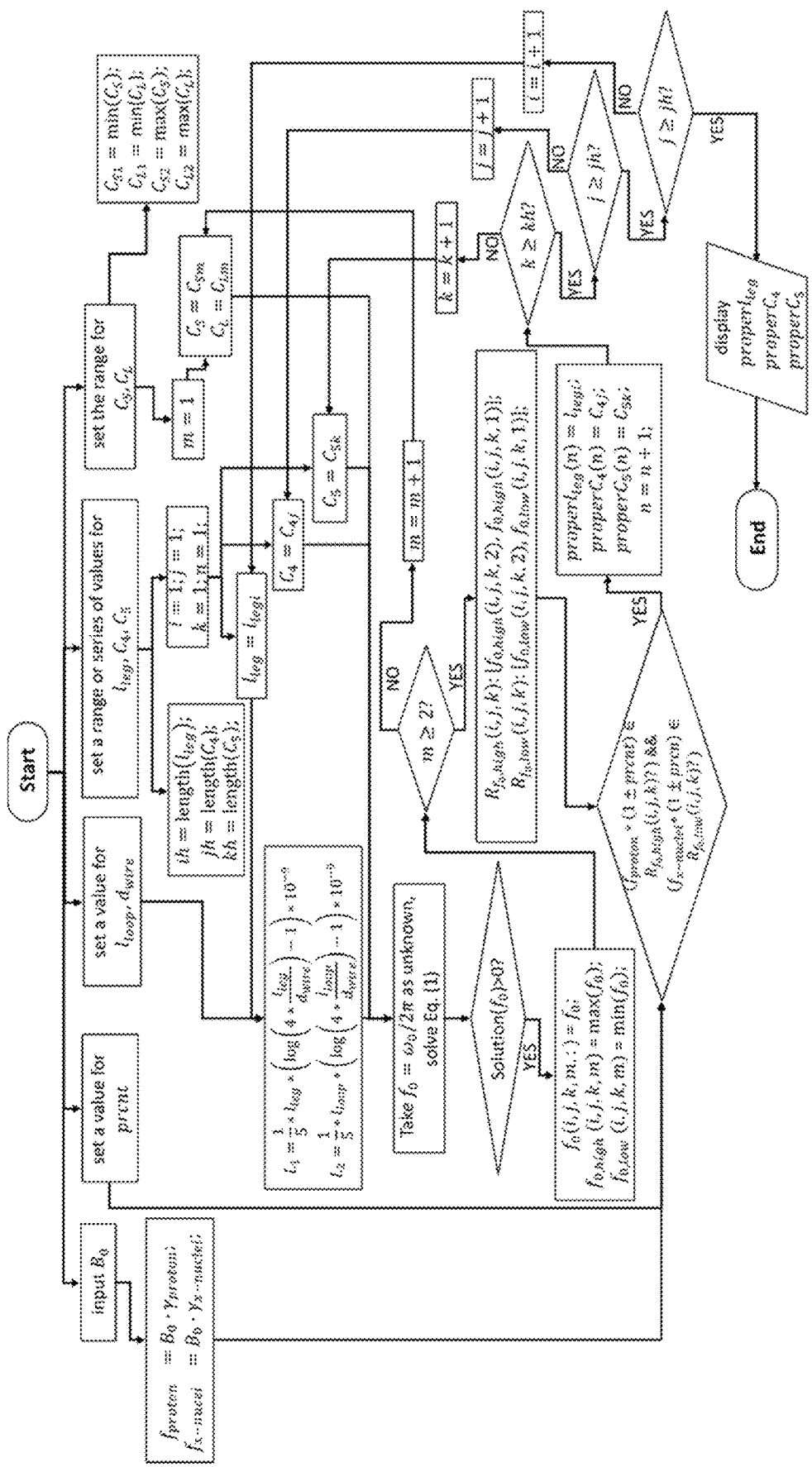
FIG. 3 is a flow chart of a non-limiting example of a process for coil design and optimization of a multi-frequency RF coil for different imaging applications.

Specifically, referring to FIG. 3, one, non-limiting example for a process for designing and simulating a multi-frequency resonant coil is provided. First, two targeted resonant frequencies for $^1$H ($f_{proton}$) and X-nuclear ($f_{(x-nucei)}$) nuclei are calculated using the static magnetic field strength ($B_0$) and gyromagnetic ratios ($\gamma_{proton}$, $\gamma_{(x-nucdei)}$) of selected nuclei (i.e., proton and X-nuclei, e.g., $^2$H or $^{17}$O nuclide). Secondly, based on the interested organ or tissue (e.g., brain) in the animal or human, the coil size and length of the coil wire ($l_{loop}$) used to shape the coil loop can be determined. The total length of two coil-legs ($l_{leg}$) and the two fixed capacitors ($C_4$ and $C_5$) can be estimated given a rough range or a set of values since it is difficult to obtain them based on prior knowledge alone. The coil leg should not be too long or too short as compared to $l_{loop}$ because a coil leg that is too long may cause significant interference to the $B_1$ field and performance of the loop coil, and a coil leg that is too short may fail to tune the coil within the targeted frequency range. Generally, $l_{leg}$ should be substantially shorter than $l_{loop}$, and both coil legs and coil loop serve as inductors. Their inductances $L_1$ and $L_2$ can be estimated from $l_{leg}$, $l_{loop}$ and the diameter of the utilized wires ($d_{wire}$) according to the equations shown in FIG. 3. $C_5$, used as a balanced matching capacitor, is usually set close to the matching capacitor $C_S$, so the range of $C_5$ can be the same as the range of the matching capacitor ($C_S$). $C_5$ can be also set equal to $C_S$ to make the simulation less time-consuming. Note that the additional $C_S$ matching capacitor could improve the coil performance, the described coil design is still functional without using $C_S$ (thus, taking the second term out from Eqn. 3). The capacitance range of variable tuning capacitor ($C_L$) and matching capacitor ($C_S$) can be selected from commercially available non-magnetic trimmer capacitors (usually with a minimum capacitance value of ~1 pF). Only the minimum and maximum capacitances are used in this non-limiting example of this flow chart calculation because the minimum of $C_L$ and $C_S$ will give the upper boundaries of both proton and X-nuclei frequencies and the maximum will determine the lower boundaries. With all these pre-settings, the boundaries can be determined by solving Eqn. 3.

The parameter, prcnt, shown in the flow chart of FIG. 3, describes the flexibility of the coil design. A higher percentage value of prcnt means more flexibility for the coil to be tuned/matched to the targeted frequencies which will give more tolerance to the frequency shift, for instance, caused by the sample loading effect. If the targeted frequencies are still within the boundaries after adding the tolerance to them, the corresponding $l_{leg}$, $C_4$ and $C_5$ and the pre-determined $d_{wire}$, $l_{loop}$, $C_L$, and $C_S$ will be regarded as appropriate values for an optimal coil design. Setting different tolerance may output different sets of $l_{leg}$, $C_4$, and $C_5$.

Figure 5A:
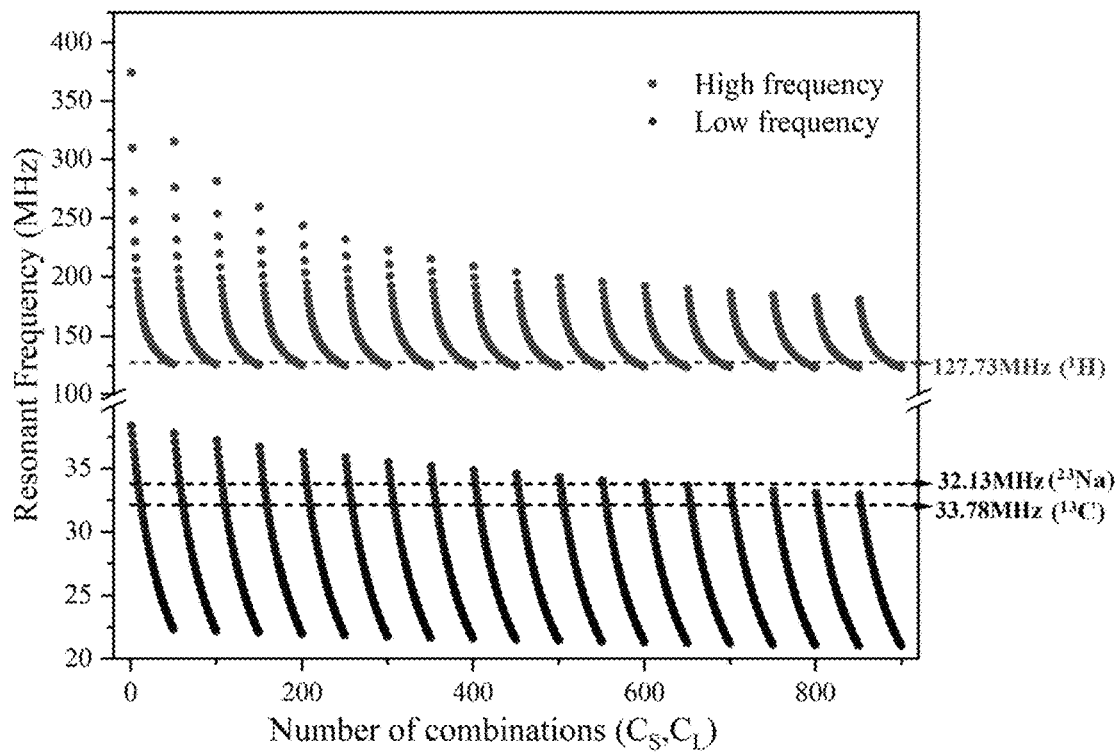
FIG. 5A shows an example to design RF coils with a larger coil diameter (15 cm) for desired human $^1H$-$^{23}Na$-$^{13}C$ MR imaging application at 3T ($^{23}Na$: sodium-23). The graph shows simulated resonant frequency ranges of the RF coil with a 15 cm diameter loop, the coil wire diameter $d_{wire}$=1.024 mm, $l_{loop}$,=15.0×π=47.1 cm, $l_{leg}$=10 cm, $C_4$=26 pF, $C_S$=25 pF, and ($C_S$, $C_L$)=1:1:50 pF. Larmor frequency at 3T is: 127.7 MHZ for $^1H$; 32.1 MHz for $^{13}C$ and 33.8 MHz for $^{23}Na$.
Figure 5B:
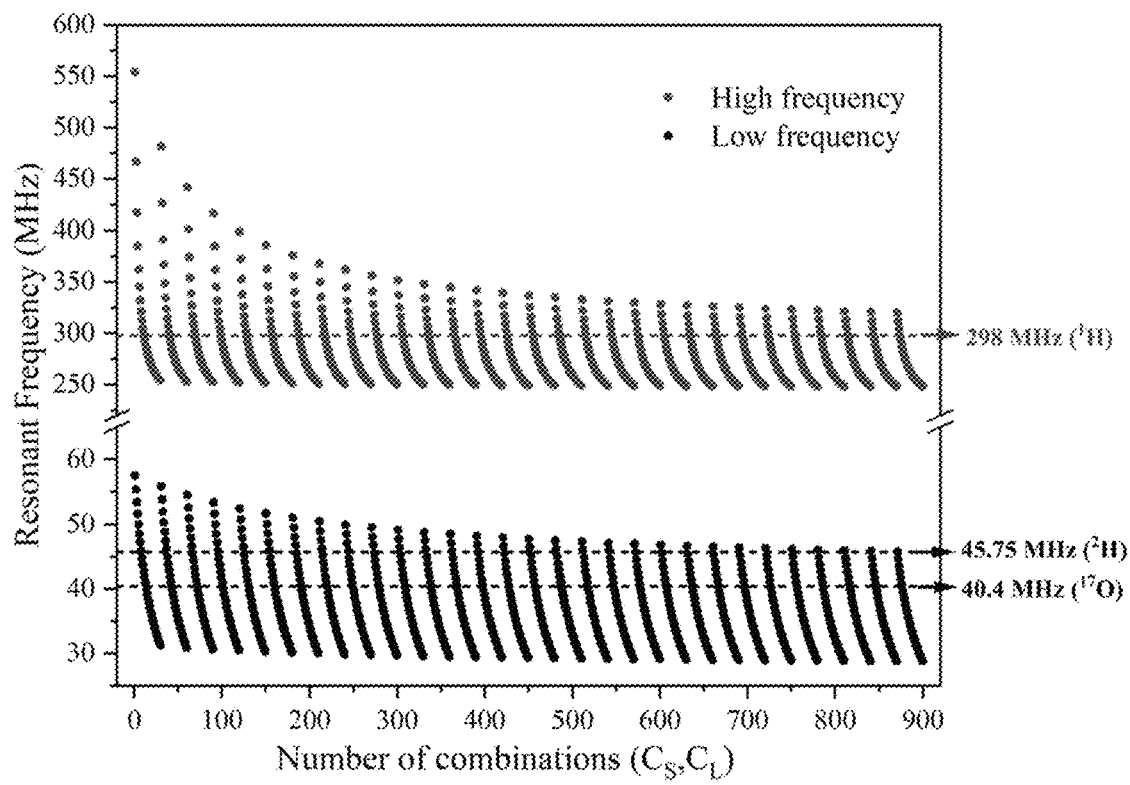
FIG. 5B is a graph of an example to design RF coils with a larger coil diameter (15 cm) for desired human $^1H$-$^2H$-$^{17}O$ MR imaging application at 7T. The graph shows simulated resonant frequency ranges of the coil with a 15 cm diameter loop, the coil wire diameter $d_{wire}$=1.291 mm, $l_{loop}$=15.0× π=47.1 cm, $l_{leg}$=6 cm, $C_4$=11 pF, $C_5$=11 pF, and ($C_S$, $C_L$)=1:1:30 pF. Larmor frequency at 7T: 298 MHZ for $^1H$; 45.75 MHz for $^2H$ and 40.4 MHz for $^{17}O$.

One non-limiting example is provided to show how a $^1$H-$^2$H dual-frequency surface coil for 16.4T imaging application was designed, and is provided with respect to FIGS. 4A-4F. This example shows how to design a $^1$H-$^2$H dual-frequency surface or local coil, which can be also tuned to $^{17}$O resonant frequency. In this non-limiting example, the RF antenna is formed with a 5-cm-diameter circular loop using an AWG-16 copper wire for animal imaging application at 16.4T. The wire diameter of AWG-16 copper wire, $d_{wire}$ is 1.29 mm. $l_{loop}$, the circumstance of the circular loop, equals to 5 cm x$\pi$=15.7 cm. $C_L$ and $C_S$ are chosen to be tunable from 1 to 23 pF. $l_{leg}$, $C_4$, and $C_5$ can be set as a series of values, $l_{leg}$=[2.0, 2.5, 3.0, 3.5, 4.0, 4.5] cm, $C_{4=1:1:10}$ pF and $C_5$=1:1:10 pF. The appropriate 48 sets of $l_{leg}$, $C_4$, and $C_5$ values are shown in FIGS. 4A-4C with prcnt set to 20%. FIG. 4A shows the total length ($l_{leg}$) of the two legs while FIGS. 4B and 4C show the corresponding $C_4$ and $C_5$ values. The number of qualified designs that the algorithm outputs depends on the setting of tolerance, prcnt. If prcnt is set to zero, the algorithm will output 419 sets of values. If it's set to 25%, it will output only 8 designs with the highest tolerance. If $l_{leg}$, $C_4$, and $C_5$ are set with a finer step instead of 5 mm, 1 pF and 1 pF, a higher number of qualified designs will be output and the plots shown in FIGS. 4A-4C will be more continuous rather than discrete, but the calculation will be much more time-consuming. The results from coarse steps actually can be useful to estimate the qualified range of these three parameters, i.e., $l_{leg}$, $C_4$, and $C_5$. For example, when the total length of the two legs is 3.5 cm, the corresponding, lowest $C_4$ is 4 pF, while $C_5$ can be any value from 1 to 10 pF. Further simulation with a finer step in $C_4$ revealed that if $C_4$ is set to be 4.7 pF, $C_5$ values should be from 1 to 4 pF. When constructing the $^1$H-$^2$H dual-frequency coil with the 5-cm-diameter loop we used 2.2 pF for $C_5$, $l_{leg}$=3.5 cm, $C_5$=2.2 pF and $C_{4=4.7}$ pF, in which the same coil can be tuned/matched to 698 MHz for $^1$H, or 107 MHz for $^2$H or 94.7 MHz for $^{17}$O application at 16.4T, with variable $C_S$ and $C_L$ from 1 to 10 pF with a step of 0.1 pF (instead of 1:0.1: 23 pF to save simulation time) as shown in FIG. 4D. The targeted frequencies, 698 MHz for $^1$H,107 MHz for $^2$H and 94.7 MHz for $^{17}$O at 16.4T, are located in favorable positions within the high- and low-frequency range. FIG. 4D also presents the coil's triple-tuning capability with an additional $^{17}$O resonance of 94.7 MHz at 16.4T. FIGS. 4E and 4F present the simulated resonant frequencies with two non-qualified $C_4$ values (1 or 15 pF), which are outside of the appropriate frequency range and therefore unable to cover both $^1$H and $^2$H or $^{17}$O resonant frequencies. FIGS. 5A and 5B illustrates an example to design optimal RF coils with a much larger coil diameter (15 cm) for desired human $^1$H-$^{23}$Na-$^{13}$C MR imaging application at 3T (FIG. 5A) and $^1$H-$^2$H-$^{17}$O MR imaging application at 7T (FIG. 5B), respectively.

MRI and X-Nuclear MRSI Experiments

Experiments using the above-described, non-limiting examples were conducted. Most of the MRI/MRSI experiments were conducted on a 16.4T/26 cm bore animal scanner (Varian/VNMRJ, California). Some MRI/MRSI experiments were conducted using a 7T/90 cm bore human whole-body scanner (Siemens, Germany).

Dual-Frequency $^1$H-$^2$H Resonant Surface Coil Versus Traditional $^1$H Resonant Surface Coil at 16.4T A $^1$H-$^2$H dual-frequency resonant surface coil was designed using the procedure described above with respect to FIG. 3. Qualified designs and their associated parameters were obtained through numerical simulations, as demonstrated in FIGS. 4A-4F. Several coils were designed and constructed with parameters provided in Table 1 and as described with respect to FIGS. 2A and 2B.

TABLE 1

Non-limiting example coil parameters.

| | Shape & Size | Capacitors | Copper Wire | Label |
|---|---|---|---|---|
| Coil A | One circular loop: dia. 5 cm; $l\text{loop} = \pi * 5$ cm; $l\text{leg} = 3.5$ cm | fixed capacitors $C_4 = 4.7$ pF and $C_5 = 2.2$ pF; variable matching capacitor $C_S = 1$-23 pF; variable tuning capacitor $C_L = 1$-23 pF | AWG16 | (A) |
| Coil B | One circular loop: dia 5 cm; $l\text{loop} = \pi * 5$ cm; | split capacitors $C_1 = C_2 = C_3 = C_4 = 1.0$ pF; fixed capacitors $C_5 = 4.7$ pF; variable matching capacitor $C_S = 1$-23 pF; variable tuning capacitor $C_L = 1$-23 pF | AWG16 | (B) |
| Coil C | Same as Coil A | Same as Coil A but $C_4$ was removed. | AWG16 | (C) |
| Coil D | Coil array composed of two Coil As | Same as Coil A | AWG16 | (D) |
| Coil E | Two turns of oval loop; major axis 2.8 cm, minor axis 2.3 cm; $l\text{loop} = 16.1$ cm; $l\text{leg} = 4$ cm | fixed capacitors C4 = 3.3 pF and $C_5 = 4.7$ pF; variable matching capacitor $C_S = 1.23$ pF; variable tuning capacitor $C_L = 1.23$ pF | AWG16 | (E) |
| Coil F | Two turns of oval loop; major axis 2.2 cm, minor axis 1.8 cm; $l\text{loop} = 12.6$ cm; $l\text{leg} = 3$ cm | fixed capacitors $C_4 = 3.3$ pF and $C_5 = 4.7$ pF; variable matching capacitor $C_S = 1.23$ pF; variable tuning capacitor $C_L = 1.23$ pF | AWG18 | (F) |
| Coil G | Coil array composed of two identical $^1$H-$^2$H-$^{17}$O coils. Each with 15 cm diameter circular loop; $l\text{loop} = 47.1$ cm; $l\text{leg} = 6.0$ cm | fixed capacitors $C_4 = 11$ pF and $C_5 = 11$ pF; variable matching capacitor $C_S = 1.23$ pF; variable tuning capacitor $C_L = 1.23$ pF | AWG16 | (G) |

The resonant frequency range calculated using Eqn. 3 with the above coil parameters covered the resonant frequencies of $^1$H at 698 MHz, $^2$H at 107 MHz, or $^{17}$O at 94.7 MHz at 16.4T, as illustrated in FIG. 4D. Coil A was tested on a vector network analyzer to measure the scattering or S parameters at 698 MHz, 107 MHz, and 94.7 MHz, and then evaluated through an imaging study at 16.4T using a 3.5 cm-diameter spherical water phantom. Global $^1$H and $^2$H FIDs were acquired using a single-pulse-acquire sequence with parameter settings shown in Table 2 after RF pulse power calibration and $B_0$ shimming. The $^1$H $B_1$ field was mapped based on the double-flip-angle method (such as described in Insko E, Bolinger L. Mapping of the radiofrequency field. journal of Magnetic Resonance, Series A 1993; 103(1):82-85., and incorporated herein by reference in its entirety) using the 2D gradient-echo (GE) multiple-slice (GEMS) imaging sequence.

TABLE 2

Non-limiting example MRI and MRS sequence parameters.

| Tested coil | Phantom/Animal | Sequence | Excitation Nuclei | Pulse | TR | | Matrix | Scan Time | Field of view |
|---|---|---|---|---|---|---|---|---|---|
| Coil A | 3.5 cm tap-water spherical ball | Single Pulse | $^1$H | 400 µs hard | 2 | s | — | — | — |
| | | | $^2$H | 200 µs hard | 100 | ms | — | — | — |
| | | | $^{17}$O | 600 µs hard | 50 | ms | — | — | — |
| | | 2D GEMS | $^1$H | 2000 µs gauss | 6 | s | 64 × 64 | 12 min 54 s | 45 × 48 mm$^2$ |
| | | 3D CSI | $^{17}$O | 200 µs hard | 50 | ms | 9 × 9 × 5 | 51.4 s | 80 × 80 × 80 mm$^3$ |
| Coil B | 3.5 cm tap-water spherical ball | Single Pulse | $^1$H | 400 µs hard | 2 | s | — | — | — |
| | | 2D GEMS | $^1$H | 2000 µs gauss | 6 | s | 64 × 64 | 12 min 54 s | 48 × 48 mm$^2$ |
| Coil C | 3.5 cm tap-water spherical ball | Single Pulse | $^{17}$O | 600 µs hard | 50 | ms | — | — | — |
| | | 3D CSI | $^{17}$O | 200 µs hard | 50 | ms | 9 × 9 × 5 | 51.4 s | 80 × 80 × 80 mm$^3$ |
| Coil D | 4.5 cm-diameter water ball containing 0.4% D2O and 77 mM NaCl | 2D GEMS | $^1$H | 2000 µs gauss | 39.5 | ms | 128 × 128 | 5.1 s | 80 × 80 mm$^2$ |
| | | 2D GEMS | $^2$H | 600 µs gauss | 70 | ms | 32 × 32 | 2 min 23 s | 80 × 80 mm$^2$ |
| | | 3D CSI | $^2$H | 200 µs hard | 45 | ms | 9 × 9 × 5 | 1 min 56 s | 80 × 80 mm$^2$ |

TABLE 2-continued

Non-limiting example MRI and MRS sequence parameters.

| Tested coil | Phantom/Animal | Sequence | Nuclei | Excitation Pulse | TR | Matrix | Scan Time | Field of view |
|---|---|---|---|---|---|---|---|---|
| Coil E | 2.5 cm tap-water | 2D GEMS | $^1H$ | 2000 µs gauss | 100 ms | 128 × 128 | 51.2 s | 30 × 30 mm$^2$ |
| | spherical ball | 3D CSI | $^2H$ | 100 µs hard | 400 ms | 9 × 9 × 5 | 3 min 26 s | 30 × 30 mm$^2$ |
| | | 3D CSI | $^{17}O$ | 100 µs hard | 50 ms | 9 × 9 × 5 | 1 min 17 s | 30 × 30 mm$^2$ |
| Coil F | Normal rat brain | 2D GEMS | $^1H$ | 2000 µs gauss | 165.9 ms | 128 × 128 | 1 min 47 s | 40 × 40 mm$^2$ |
| | | 3D CSI | $^2H$ | 200 µs hard | 45 ms | 9 × 9 × 5 | 1 min 56 s | 40 × 40 mm$^2$ |
| | Tumor rat brain | 2D FSEMS | $^1H$ | 200 µs SGLsinc | 2 s | 192 × 192 | 9 min 40 s | 28 × 28 mm$^2$ |
| | | 3D CSI | $^2H$ | 100 µs hard | 45 ms | 17 × 17 × 5 | 1 min 46 s | 28 × 28 mm$^2$ |
| Coil G | 15 cm-diameter water ball with 50 mM NaCl | 3D MPRAGE | $^1H$ | | 1.04 s | 192 × 192 × 64 | 4 min 31 s | 192 × 192 × 192 mm$^3$ |
| | | 3D CSI | $^{17}O$ | 500 µs hard | 50 ms | 9 × 9 × 7 | 1 min 57 s | 192 × 192 × 192 mm$^3$ |

Figure 2D:
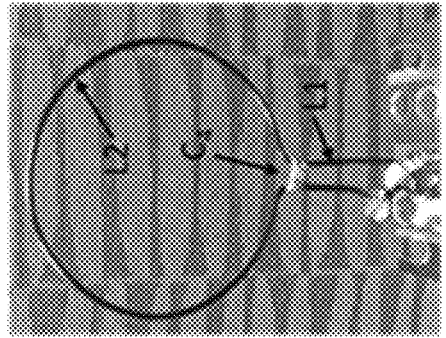
FIG. 2D is an image of a traditional $^1H$ single-frequency surface coil with three split capacitors and the same coil size as the coil of FIG. 2A.
Figure 2E:
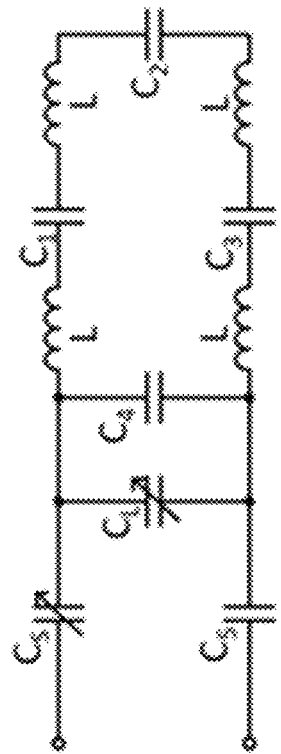
FIG. 2E is a circuit diagram of the coil of FIG. 2D.
Figure 2F:
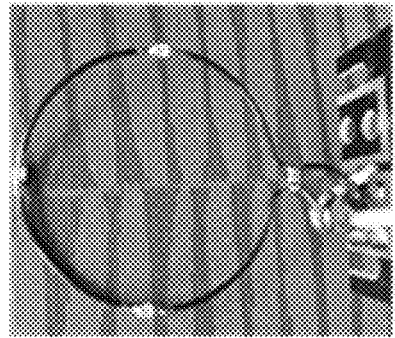
FIG. 2F is a graph of the global $^1H$ FID signal acquired using the coil of FIG. 2D.

In order to evaluate the performance of Coil A (FIG. 2A) operated at proton frequency, a traditional $^1H$ surface coil (Coil B, FIG. 2D and FIG. 2E) was built with parameters shown in Table 1. The global $^1H$ FID and proton $B_1$ maps were obtained using the same water phantom and identical imaging acquisition parameters shown in Table 2. A traditional $^{17}O$ surface coil (Coil C, Table 1) was built to evaluate Coil A's performance at X-nuclear frequency by comparing global $^{17}O$ FIDs and $^{17}O$ $B_1$ maps obtained using these two coils. All the three coils (Coil A, Coil B and Coil C) were tested for the unloaded/loaded Q factors on the network analyzer.

RF simulations were conducted to compare $B_1$ distributions and surface current densities of Coil A and Coil B at proton resonant frequency at 16.4T, and $B_1$ distributions of Coil A and Coil C at $^{17}O$ resonant frequency at 16.4T using CST studio suite 2020 (Dassault Systemes, Vélizy-Villacoublay, France) based on the hexahedral time-domain solver. The phantom and copper wire were constructed to match the experimental setup (water phantom, permittivity E=84, conductivity=0.112 S/m; copper wire, conductance=5.96×10$^7$ S/m). An isotropic resolution (0.5 mm) mesh was used for the models and boundary space.

Multi-Frequency $^1H$-$^2H$ Resonant Coil Array Design, Construction, and Evaluation at 16.4T To evaluate the multi-frequency resonant coil array design, we built a quadrature coil array, as illustrated in FIG. 6A (Coil D) comprising two identical dual-frequency $^1H$-$^2H$ surface coils, as shown in FIG. 2A. The S parameters were measured on a bench under loaded condition. 2D GEMS and 3D chemical shift imaging (CSI) sequences were respectively applied to acquire proton and deuterium images at 16.4T. All the CSI data matrices shown in this work were interpolated from 9×9×5 to 17×17×5 for display. 2D-GEMS (Table 2) deuterium images were also collected.

Multi-Frequency, Switchable, Resonant Coil Design, Construction, and Phantom Test at 16.4T Based on the multi-frequency resonant coil design, an oval-shaped multi-frequency $^1H$-$^2H$-$^{17}O$ surface coil was constructed (Coil E, Table 1) to demonstrate the possibility for operating at triple resonant frequencies via a phantom study at 16.4T. 2D $^1H$ GEMS, 3D $^2H$ CSI, and 3D $^{17}O$ CSI data were acquired after manually tuning/matching the coil to the $^1H$, $^2H$, or $^{17}O$ frequencies, respectively. The main parameters are provided in Table 2.

In Vivo Test of the Dual-Frequency Resonant Coil in Rat Brain at 16.4T

Another example of $^1H$-$^2H$ dual-frequency resonant coil (Coil F, Table 1) with two turns of an oval-shaped loop was constructed and evaluated in two rat brain studies at 16.4T, one with a normal rat and the other on a rat with a brain tumor. Both animals were under 2% isoflurane anesthesia. For the normal rat brain study, after RF power calibration and $B_0$ shimming at $^1H$ frequency, a 2D GEMS sequence was used to acquire proton MRI images. The coil was then re-tuned/re-matched to the $^2H$ frequency without changing the coil and sample (i.e., rat brain) positions. After RF pulse power calibration, 3D $^2H$ CSI data were acquired. For the tumor rat brain study, deuterated glucose (D-Glucose-6,6-$d_2$) was administered via a 2 min intravenous infusion. A 2D fast spin-echo multiple-slice (FSEMS) imaging sequence was used to acquire the anatomical brain images before the infusion. 3D $^2H$ CSI data were acquired before, during, and after the infusion at 16.4T. The main parameters are provided in Table 2. The animal experiments were conducted strictly in accordance to the Guide for the Care and Use of Laboratory Animals by the National Research Council, the protocol was approved by the Institutional Animal Care and Use Committee of the University of Minnesota.

Multi-Frequency Human Head-Size Resonant Coil Design, Construction, and Evaluation at 7T Based on the multi-frequency resonant coil design (FIG. 5B), two identical multi-frequency coils with tripe resonant frequency ($^1H$-$^2H$-$^{17}O$) tuning ability (Coil G, Table 1) were designed and constructed for human brain imaging at 7T. The two coil loops were partially overlapped to create a well-decoupled quadrature coil array. The corresponding S-parameters were measured under loaded conditions (15 cm-diameter water ball with 50 mM NaCl). We also conducted a phantom imaging test using the coil array. 3D MPRAGE and 3D$^{17}O$ CSI sequences were applied to acquire proton MRI and $^{17}O$ CSI data, respectively, on the 7T human scanner where the parameters are provided in Table 2.

Results

Simulation-Guided Coil Design for 16.4T Imaging Applications

The procedure for designing a multi-frequency surface coil, as shown in the flow chart in FIG. 3, is to solve Eqn. 3 for achieving the desired resonant frequencies (for $^1H$ and X-nuclear). For a $^1$H-$^2$H surface coil with a 5 cm-diameter loop using AWG 16 copper wires for MRSI applications at 16.4T, for example, there are many qualified designs, as shown in FIGS. 4A and 4C). Herein, $C_5$=2.2 pF, $l_{leg}$=3.5 cm, and $C_{4=4.7}$ pF were selected for the actual coil (Coil A) considering the availability of the capacitors in the lab and the convenience of having coil legs that were not too short for the coil construction. FIG. 4D shows the resonant frequency range over which the unloaded $^1$H-$^2$H dual-frequency single-loop coil can be tuned/matched with variable $C_L$ and $C_S$ from 1 to 10 pF in intervals of 0.1 pF. Both targeted frequencies, 698 MHz for $^1$H and $10^7$ MHz for $^2$H at 16.4T, are located in favorable positions in the high- and low-resonant frequency ranges (FIG. 4D). This figure also presents the triple-tuning capability of the coil with an additional operation frequency for $^{17}$O MRSI at 94.7 MHz at 16.4T. FIGS. 4E and 4F present the simulated resonant frequencies with two non-qualified $C_4$ values (1 and 15 pF) that are outside the appropriate frequency range and therefore unable to cover both the $^1$H and the $^2$H or $^{17}$O resonant frequencies.

FIGS. 5A and 5B are further graphs showing additional circuit designs for particular resonant frequencies at a given magnetic field strength with a large coil size.

In particular, FIG. 5A shows the resonant-frequency range that the 15-cm diameter loop coil can reach, covering the Larmor frequencies for human $^1$H, $^{23}$Na, and $^{13}$C imaging applications at 3T.

One set of the coil parameters is listed as follows through calculations. In particular, parameters were:
  Loop diameter=15 cm;
  Number of loops=1;
  Total length of two legs (related to L1)=10 cm;
  Each leg 5 cm long;
  Copper wire=AWG-18;
  $C_5$=25 pF;
  $C_{4=26}$ pF;
  $C_S$=1~50 pF tunable; and
  $C_L$=1~50 pF tunable.

FIG. 5B shows the simulation results of an example for designing a 15-cm diameter coil covering the Larmor frequencies for $^1$H, $^2$H, and $^{17}$O at 7T. One set of coil parameters is listed as follows through calculations. In particular, parameters were:
  Loop diameter=15 cm;
  Number of loops=1;
  Total length of two legs (related to $L_1$)=6 cm;
  Each leg 3 cm long;
  Copper wire=AWG-16;
  $C_{5=11}$ pF;
  $C_{4=11}$ pF;
  $C_S$=1-30 pF tunable; and
  $C_L$=1-30 pF tunable.

$^1$H Imaging Comparison of Dual-Frequency Surface Coil (Coil A) with Traditional Single-Loop $^1$H/$^{17}$O Surface Coil (Coil B/Coil C) at 16.4T The voltage reflection coefficients of three coils (Coil A, Coil B and Coil C) at different resonate frequencies were studied with unloaded and (light) loaded Q factors. The ratios of unloaded and loaded Q factors of Coil A were 1.33 for $^1$H, 1.64 for $^2$H and 1.54 for $^{17}$O, while Q ratio of Coil B for $^1$H was 1.47 and that of Coil C for $^{17}$O was 1.47; they were similar among the three coils. The Q ratio was quite low due to the light loading of the phantom. Using a high loading phantom (5.5 cm diameter sphere with DI water and 86 mM NaCl), the ratios of unloaded and loaded Q factors increase dramatically.

Figure 7B:
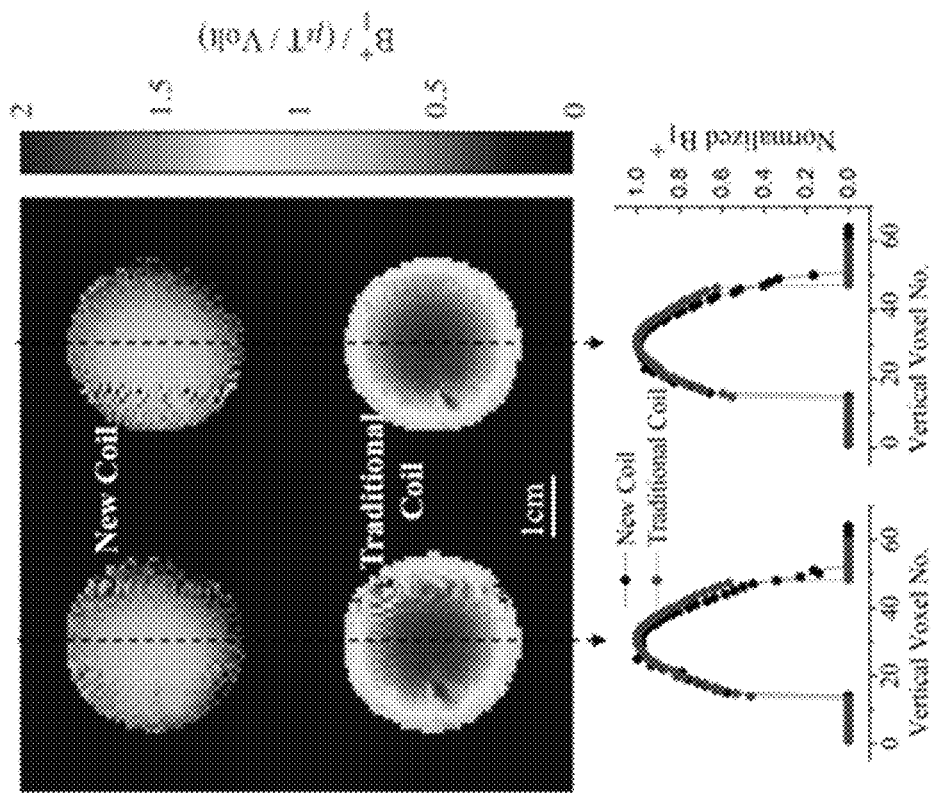
Figure 7A:
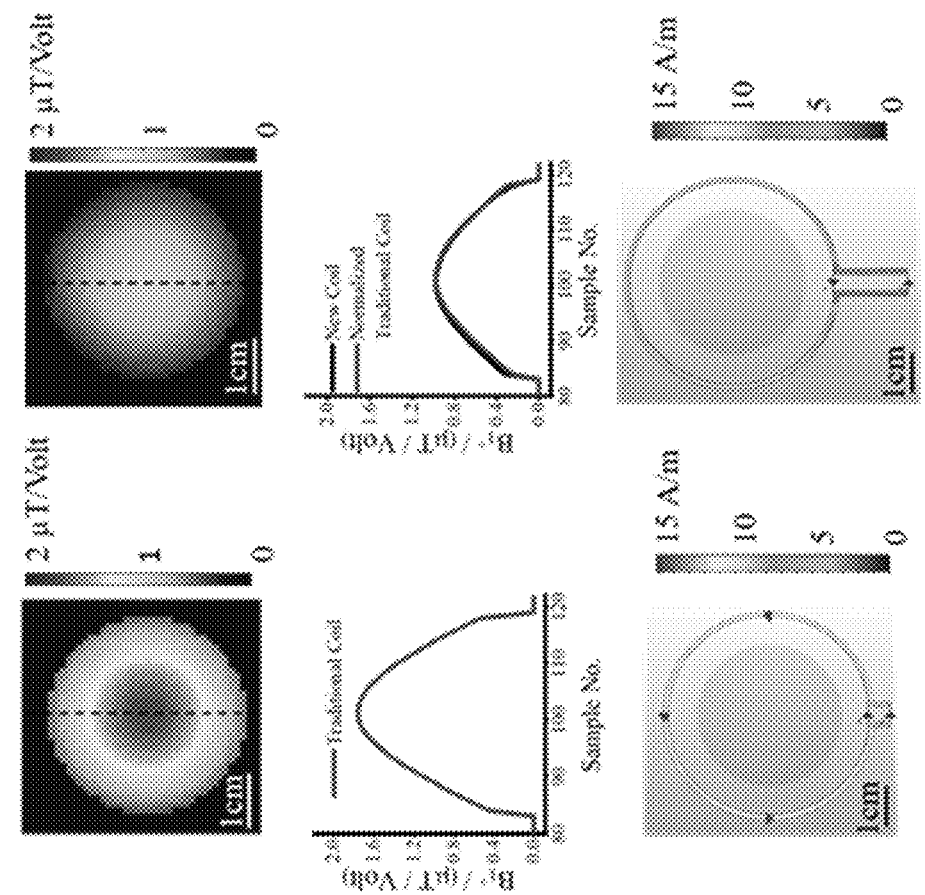
FIG. 7A is a set of graphics showing simulation results: comparing coronal $B_1$ field distribution (top), central $B_1$ profile (middle), coil wire current distribution (bottom), between the traditional $^1H$ single frequency coil (FIG. 2D) and the dual-frequency coil (FIG. 2A) operating at $^1H$ frequency at 16.4T.

FIG. 7A shows the simulated coronal $B_1$ maps and profiles, and current distributions of Coil A and Coil B at the proton frequency (698 MHz at 16.4T), while the measured coronal proton $B_1$ distributions of both coils are shown in FIG. 7B. Both simulation and experiment show the proton $B_1$ strength of Coil A reduces about half compared with Coil B, however, the $B_1$ distributions for both coils are almost identical (FIG. 7). The simulated current distributions of both coils along the coil loop at the proton frequency show a high similarity, though there is a significant current trapped in the small leg loop of Coil A. Simulated and measured coronal $B_1$ distributions at $^{17}$O frequency of Coil A and Coil C indicate similar $B_1$ strength and spatial distribution between the two coils and excellent agreement between the experimental and simulated results.

Dual-Frequency $^1$H-$^2$H Resonant Coil Array Construction and Evaluation at 16.4T Coil D is shown in FIG. 6A. The table in FIG. 6B summarizes the S parameters of the two-coil array driven in quadrature mode at $^1$H and $^2$H frequencies under the loaded condition. The voltage reflection coefficients of each channel (or each coil), that is, S11 and S22, were −25 dB at the $^2$H resonant frequency of $10^7$ MHz and −36 dB at the $^1$H resonant frequency of 698 MHz for Channel 1, respectively, and −26 dB at $10^7$ MHz and −44 dB at 698 MHz for Channel 2, respectively. S21, which reflects the decoupling efficiency of the two coils, was −15 dB at $10^7$ MHz and −46 dB at 698 MHz. FIGS. 6C and 6D display the phantom test results obtained using Coil D. FIG. 6C shows a representative deuterium GEMS image (sagittal orientation) and FIG. 6D shows a representative $^2$H CSI image (axial orientation,) which is overlaid on the corresponding proton GEMS image measured using the same coil array. Both the $^2$H GEMS and CSI images have similar signal distributions, as anticipated.

Figures 8A, 8B:
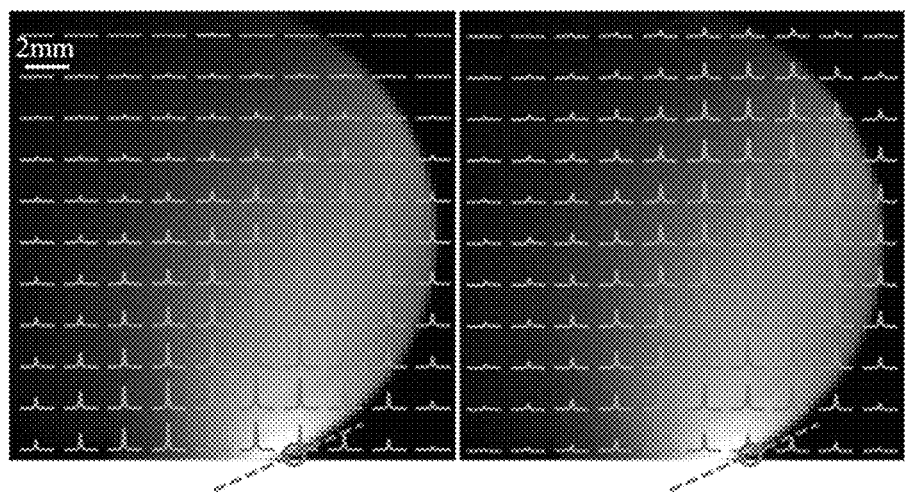
FIG. 8A is a representative axial $^{17}O$ CSI image overlaid on the corresponding proton image acquired using the same multi-frequency RF coil from a water phantom.
FIG. 8B is a representative axial $^2H$ CSI image overlaid on the corresponding proton image acquired using the same multi-frequency RF coil from a water phantom to demonstrate the triple resonant frequency tuning ability of the coil design in accordance with the present disclosure.

Multi-Frequency $^1$H-$^2$H(-$^{17}$O) Resonant Coil (Coil E/Coil F) Construction and Evaluation at 16.4T Coil E was constructed to demonstrate the triple-tuning ability of the new coil design via a phantom imaging experiment at 16.4T. FIGS. 8A and 8B show the representative $^{17}$O (FIG. 8A) and $^2$H (FIG. 8B) water CSI slices overlaid on the corresponding $^1$H GEMS image acquired using the same resonant coil (Coil E). The images indicate an excellent signal-to-noise ratio (SNR) and similarity between the $^{17}$O and $^2$H signal distributions, and the same coil can be operated at three ($^1$H, $^2$H and $^{17}$O) selected resonant frequencies.

Figures 9A, 9B:
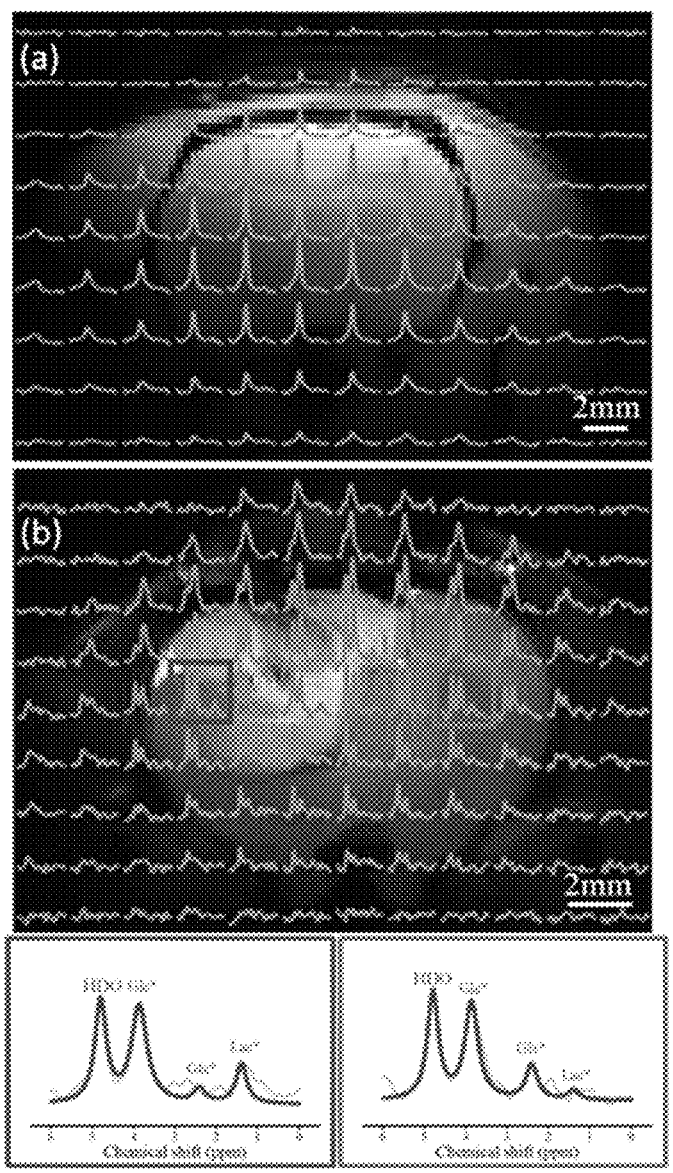
FIG. 9A is a representative axial $^2H$ CSI images overlaid on the corresponding proton anatomical images obtained from the anesthetized normal rat brain.
FIG. 9B is a representative axial $^2H$ CSI images overlaid on the corresponding proton anatomical images obtained from the anesthetized tumor rat brain and associated graphs using a $^1H$-$^2H$ dual-frequency coil. The $^2H$ CSI data were acquired around 25 min after a D-Glucose-6,6-$d_2$ infusion. The graphs show the deuterium spectra from two different voxels in the tumor rat brain, i.e., tumor voxel in red and normal-appearing voxel in green. The grey line is the original spectrum while the red line is the spectrum fitted with a Lorentzian lineshape in which the deuterium-labeled water (HDO) peak at the chemical shift of 4.8 ppm, deuterium-labeled glucose (Glc*) peak at 3.87 ppm, deuterium-labeled glutamine/glutamate (Glx*) peak at 2.4 ppm, and deuterium-labeled lactate (Lac*) peak at 1.4 ppm can be easily identified.

Coil F was constructed for in vivo $^2$H MRSI of normal and tumor rat brains. The results of representative $^2$H CSIs overlaid on the corresponding $^1$H images are shown in FIGS. 9A (in normal brain) and 9B (with brain tumor). The proton image covers the entire rat brain, including the sub-cortical regions with the in-plane resolution of 0.3×0.3 mm$^2$. The $^2$H CSI of the normal rat (FIG. 9A) with the nominal resolution of 4.4×4.4×8 mm$^3$ and 69 s total imaging acquisition time shows an excellent SNR of natural abundance deuterium water (HDO) signal in the brain. A higher spatial resolution can be achieved by reducing the field of view (FOV) or increasing the number of phase-encoding steps. The $^2$H CSI data shown in FIG. 9B was acquired 25 min after administering deuterium-labeled glucose (D-Glucose-6,6-d$_2$) in the rat with brain tumor and had a higher nominal resolution of 1.6×1.6×4.8 mm$^3$ (approximately 13 times higher than that shown in FIG. 9A) acquired over 105 s of total imaging acquisition time. The $^2$H MR spectra of the voxels taken from the tumor (red box) and the normal-appearing tissue (green box) clearly show that the deuterium-labeled glutamine/glutamate (Glx*) peak in the normal-appearing tissue was significantly higher than that in the tumor, while the deuterium-labeled lactate (Lac*) peak was much higher in the tumor region. This phenomenon is known as the Warburg effect and reflects the abnormal glucose metabolism in brain tumors.

Figure 10E:
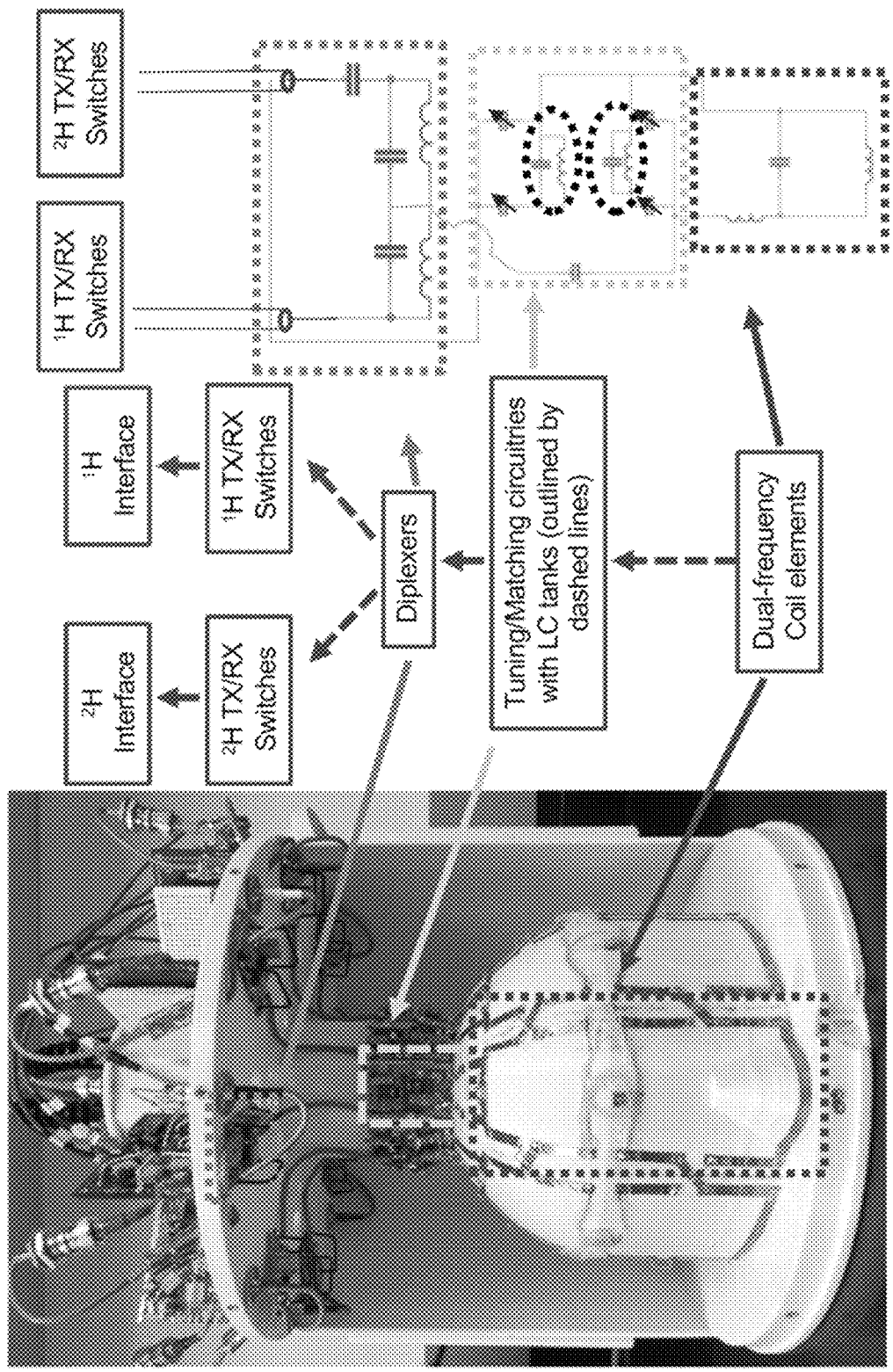
FIG. 10E is an image of constructed 8-channel $^1$H-$^2$H dual-frequency head coil array for human brain imaging application at 7T, and a schematic of coil design and interface for a representative coil channel. Overlapped coil structure is applied to decouple broadband interference among adjacent coils. LC tank circuitry blocked $^1$H frequency signal which allows fine-tuning and matching at $^2$H frequency without interference to the tuning and matching of $^1$H frequency, thus, ensuring that the coil array can be tuned and matched to two resonant frequencies: $^1$H and $^2$H Larmor frequency, respectively. Diplexers divide the signal from the end of tuning circuitries into $^1$H frequency route and $^2$H frequency route to $^1$H T/R switches and $^2$H T/R switches.

Dual-Frequency $^1$H-$^2$H($^{17}$O) Resonant Coil Construction and Evaluation (Coil G) on 7T Human MRI Scanner To illustrate the potential of the new dual-frequency coil design for translation and clinical diagnosis, we also designed and constructed a human head-size multi-frequency transceiver coil array (Coil G, as shown in FIGS. 5B and 10A) for $^1$H MRI (298 MHz) and $^2$H (45.8 MHz) or $^{17}$O (40.4 MHz) MRSI applications at 7T based on the same coil design principle and the flow chart of FIG. 3. FIG. 10B shows the S11 and S12 measurement results from the two coil channels under loaded conditions in which high-quality resonance peaks for all three $^1$H-$^2$H-$^{17}$O nuclide applications are clearly seen. The RF coil array was further evaluated in a 7T human scanner using a human head-sized spherical phantom containing water. The proton anatomical image (FIG. 10C) and $^{17}$O CSI (FIG. 10D, naturally abundant H$_2^{17}$O signal) were acquired using the same coil array but with different T/R switches. Note that the intensity of the proton image is spatially inhomogeneous because of the large imaging object and coil size, and static wave behavior at a high $^1$H resonant frequency of 298 MHz. In contrast, $^{17}$O CSI achieved excellent spatial coverage and relatively uniform sensitivity across the entire phantom, even when only two coil channels were applied. Adding more array channels should further improve the sensitivity, coverage, and signal uniformity for both proton and X-nuclei imaging applications. FIG. 10E shows a prototype of 8-channel $^1$H-$^2$H dual frequency human head coil with advanced tuning/matching circuits and T/R switches for 7T imaging application.

DISCUSSION

In the above examples, simple surface coil circuits with multi-frequency tuning capability were provided illustrating the design and performance of multi-nuclear RF coils. That is, the design process was evaluated by constructing several prototype coils with various coil sizes that are tunable to the $^1$H, $^2$H, and/or $^{17}$O resonant frequencies for 16.4T animal and 3T or 7T human MR imaging applications. These coils were evaluated by obtaining proton MRI, $^2$H and $^{17}$O CSI data in phantom tests at 16.4T/7T and in vivo rat brain studies at 16.4T. Two-channel dual-frequency $^1$H-$^2$H or $^1$H-$^{17}$O coil arrays were also constructed and tested to demonstrate the feasibility of using the same design principle to build multi-frequency and multi-coil arrays covering larger sample regions for multi-nuclei imaging applications.

Compared with prior attempts at multiple resonance coil designs, the coil design process and the examples provided above is substantially simpler and can be designed to include an extra capacitor (C$_4$) and inductor L$_1$ to the traditional surface coil circuit, as illustrated in FIGS. 2A and 2B. Additionally, this design allows a single coil to be tuned and matched to cover a very large frequency range, for example, from the extremely high resonant frequency of 1200 MHz to the low frequency of 100 MHz (a 12-fold frequency or >1000 MHz difference) with C$_{4=1}$ pF for the 5 cm-diameter loop coil, as shown in FIG. 4E. Taking the traditional proton surface coil (shown in FIGS. 2D and 2E) as an example, if all the split capacitors (C$_1$, C$_2$, C$_3$) were removed and the value of C$_4$ kept at 1 pF or higher, the coil resonance frequency could not exceed 240 MHz owing to the relatively large coil size (5 cm diameter using 16-AWG copper wire) for 16.4T $^1$H imaging applications. The addition of split capacitors not only increases the resonant frequency, but also induces circuit complexity and makes it difficult to reach low-γ X-nuclear resonant frequencies using the same loop coil, thus, the dual-coil device (i.e., $^1$H coil(s) plus X-nuclear coil(s)) is commonly designed with complexity, high cost and mutual coupling issue. In contrast, the coil design of the present disclosure reduces the complexity. By introducing C$_4$ and two-coil leg wires of a selected length (which serve as a small inductor L$_1$ of, e.g., approximately 26 nH for the coil shown in FIG. 2A) between the traditional LC resonant loop and the tuning/matching circuit, two resonant frequencies across a very large range can be generated for the same RF coil with an adequate tuning/matching range for each resonant frequency (FIGS. 4 and 5).

The dual-frequency $^1$H-$^2$H surface coil based on the new design generates a relatively weaker but adequate proton B$_1$ field (or detection sensitivity), but a similar B$_1$ or signal distribution as a conventional $^1$H coil for $^1$H MRI and B$_0$ shimming serving for most X-nuclear MRSI applications. Its performance for $^1$H applications is comparable to or even better than that of a traditional $^1$H transceiver volume coil because the B$_1$ field of a volume coil is usually 2-3 times weaker than that of a coil array made of multiple surface coils close to the imaging object. It can also provide a similar X-nuclear detection sensitivity and signal distribution as a traditional X-nuclear coil. When comparing proton B$_1$ field with X-nuclear B$_1$ field from the same dual-frequency coil, we found a stronger B$_1$ field (in the absolute scale) at low-γ X-nuclear frequency as well as a significant difference between proton and $^{17}$O B$_1$ spatial distributions at ultrahigh field. In spite of the difference in the B$_1$ distributions between $^1$H and low-γ X-nuclides, their imaging coverages are generally similar between the $^1$H and $^2$H or $^{17}$O images because the images are acquired from the same RF coil or array (see FIGS. 6D, 8, 9 and 10). One reason for the weak $^1$H B$_1$ field observed in the new coil design is because the small loop composed of two coil legs (L$_1$), C$_4$, and C$_L$, locally captured a significant portion of the B$_1$ field at a higher resonant frequency (i.e., $^1$H); therefore, the $^1$H B$_1$ field in the main RF coil loop (L$_2$) was reduced. One way to optimize the coil performance is to twist the two electrically insulated coil legs to cancel the local $^1$H B$_1$ field trapped in the small loop, thus, to enhance the $^1$H B$_1$ field and image quality of the large coil loop.

When combined with the multi-coil array approach, the multi-frequency coil array design of the present disclosure achieves a larger imaging coverage and higher SNR, which is important for X-nuclear applications. The results obtained from the dual-frequency quadrature coil array for the animal MR imaging application at 16.4T (e.g., FIG. 6) and the human MR imaging application at 7T (e.g., FIG. 10) indicate that multiple channels in an array can be well decoupled and each channel can be well tuned or matched to the desired resonant frequencies. Phantom tests confirmed the excellent performance and large imaging coverage of the multi-frequency coil array. It is interesting to note that the signal distributions of $^1$H MRI and $^2$H MRSI, as shown in FIG. 6D, are similar but not identical, with more proton signals obtained at the center of the phantom farther away from the coil. This is due to the well-known wave behavior at UHF, which is more pronounced for a very high $^1$H resonant frequency (698 MHz) with a relatively large coil size (5 cm diameter). This observation confirmed that although the $^1$H transmission efficiency of the $^1$H-$^2$H dual-frequency coil is lower than that of the traditional $^1$H coil, a significant portion of the RF energy is still deposited in the main RF coil loop; thus, the $^1$H imaging of a large object of interest coincides with the targeted region of the X-nuclear imaging.

The overall results and findings from these studies indicate that the multi-frequency coil design provided herein provide optimal performance for low-frequency X-nuclear (e.g., $^2$H and/or $^{17}$O) resonators and suboptimal performance for high-frequency $^1$H resonators (6-7 times higher than $^2$H or $^{17}$O) for UHF multi-frequency imaging applications. This robust coil design allows one to build large-size coils (e.g., 5 cm diameter loop coils) that can reach the extremely high resonant frequency of 1200 MHz (see FIG. 4E) without using split capacitors for potential UHF $^1$H MRI applications beyond 16.4T, or ≥15 cm diameter coils for human brain applications at 7T. This coil design for multi-nuclei applications (e.g., $^1$H, $^2$H, $^{13}$C, $^{23}$Na, $^{31}$P, and $^{17}$O nuclei, etc.) significantly simplifies the coil fabrication, minimizes the space occupied by the coil(s), and intrinsically eliminates the EM coupling between multi-nuclide frequencies or multi-coils in an array, which is especially important for human brain X-nuclear studies with whole-head coverage, commonly requiring more array coils resulting in a challenge to decouple $^1$H and X-nuclear channels. Finally, the coil design provided herein is also valid for the design of multiple-turn surface coil(s), as demonstrated herein (Coil E and Coil F). The multi-frequency coils shown in this work still need manual tuning and matching from $^1$H resonant frequency to $^2$H or $^{17}$O resonant frequency, however, new technique has been developed for auto tuning/matching using active tuning or detuning circuitry, which has been reported and will be discussed below.

The non-limiting examples provided herein present a simple and cost-effective RF coil technique for the construction of multi-frequency resonant surface coils or arrays operating at proton and X-nuclear Larmor frequencies as compared to the traditional coil design. Prototype coils were built to demonstrate the proof-of-concept via phantom tests and in vivo rat brain studies at 16.4T and bench/phantom tests targeting human head $^1$H-$^2$H-$^{17}$O imaging applications at 7T. The results confirmed the feasibility and prospects of constructing a high-channel count and dual- or triple-frequency transceiver coil array based on the new coil concept and simulation procedure, which should be advantageous for realizing high-performance X-nuclear MRS and imaging with a large-volume coverage. Finally, the same multi-frequency coil design can be applied for other X-nuclear MRS and MRSI applications, for example, the design of a triple-frequency $^1$H-$^{13}$C-$^{23}$Na resonant coil(s) or array because the $^{13}$C and $^{23}$Na nuclei have a small difference in their Larmor frequencies (e.g., for 3T application as shown in FIG. 5A). It is also possible to design multi-frequency RF coil covering multiple X-nuclei, for instance, $^{31}$P (high resonant frequency) versus $^2$H or $^{17}$O (approximately three times low resonant frequency). The coil application can also be extended to tissues or organs other than the brain.

Electronically Switchable Multi-frequency Coil Design for Multi Nuclei Imaging Application.

As discussed above, the systems and methods described herein can be applied to a variety of coil designs and clinical applications. For example, as described, data were acquired using the coil described above for each of the $^1$H, $^2$H, and $^{17}$O frequencies (e.g., FIG. 8). These concepts can be applied to yield a multi-frequency coil, such as for tri-frequency coil operation. However, the switching from one resonant frequency to another resonant frequency requires manual returning and rematching of the same RF coil. This could be not convenient or ineffective for practical application or imaging diagnosis, especially when dealing with a coil array with a high number of channels.

Figure 11:
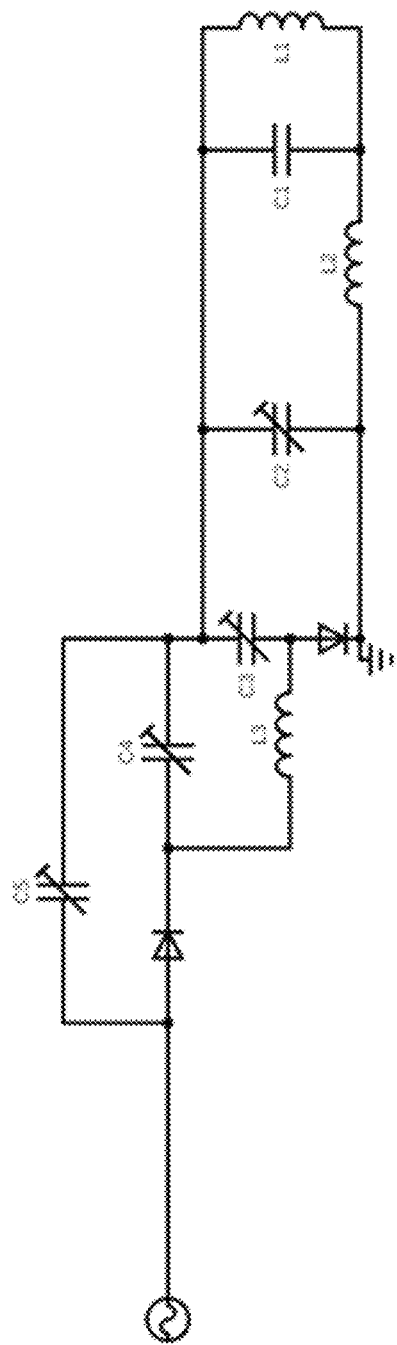
FIG. 11 is a circuit diagram of a multi-tuned coil design. For proton (no DC voltage applied for the PIN didoes), modulate $C_2$ and C5 to tune and match to 698 MHz. For $^2$H (no DC) tune and match C2 and C5 to 107 MHz. For $^{17}$O, make sure setup for $^2$H is established, apply DC voltage and modulate C3 and C4 to tune and match to 94 MHz. Therefore, controlling the PIN didoes can make the coil operated at $^2$H and $^{17}$O resonant frequency in an interleaved manner.
Figure 12:
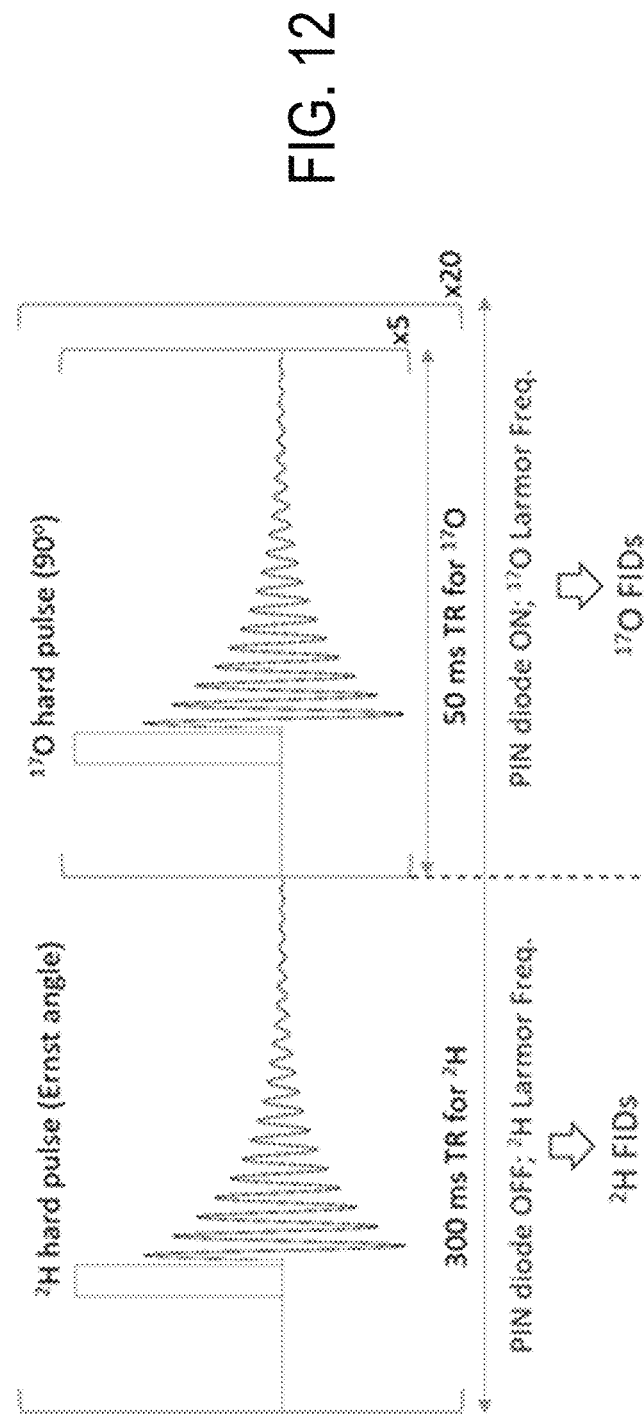
FIG. 12 is a set of correlated drawings of modified RF pulse sequence and sequence parameters for interleaved acquisition of $^{17}$O and $^2$H MRS signals using the same RF coil of FIG. 11.

To achieve rapid and electronically retuning/rematching between two desired resonant frequencies (e.g., $^1$H versus $^2$H, or $^1$H versus $^{17}$O, or $^2$H versus $^{17}$O), the disclosure coil design as illustrated in FIG. 2B was reworked as shown in FIG. 11, in which two additional variable capacitors ($C_4$ and $C_3$) with PIN diodes in serious were included for electronically retuning (by adding $C_3$) and rematching (by adding $C_4$) when the PIN diodes were turned on by the DC voltage and TTL trigger controlled by MR imaging scanner. The time to electronically switch the multi-frequency coil between two desired resonant frequencies is determined by the PIN diode on and off time which is very short (<<1 ms). For an un-limiting example, using PIN diodes and feeding the coaxial line with RF and DC powers, one can bias diodes and run RF through parallel capacitors to add capacitance in tuning and matching capacitors to drop the resonant frequency from 107 MHz ($^2$H) to 94 MHz ($^{17}$O) (FIG. 11), thereby providing an active tuning/matching between the interleaved $^2$H and $^{17}$O FID signal measurements as demonstrated in FIG. 12. Tuning and matching of $^1$H and $^2$H can be also performed automatically using the RF coil circuit shown in FIG. 11 or manually using the RF coil circuit shown in FIG. 2B. The circuit in FIG. 11 was modeled in Keysight's ADS RF simulation software selecting component values that minimized reflection coefficients at the three desired ($^1$H, $^2$H and $^{17}$O) resonant frequencies for this particular design. The circuit was built to specification, traps were added to minimize coaxial line distortion and the loaded circuit was validated on a network analyzer measuring reflection coefficients.

The new coil was tested at 16.4T (Varian, CA) with a phantom (2 cm diameter ball filled with deionized water). The $^1$H MRI was acquired using 2D GEMS sequence (TR/TE=100/4 ms, FA=20°, FOV=30 mm×30 mm, matrix=128×128) after power calibration and $B_0$ shimming. The $^2$H FID (TR=300 ms, 20 number of averages (nt), spectral width (SW)=4006.4 Hz, acquisition time (at)=44 ms, 200 µs hard pulse at Ernst pulse flip angle) and $^{17}$O FIDs (TR=50 ms, nt=100, sw=4006 Hz, at=44 ms, 200 µs hard pulse) were acquired with single-pulse-acquire sequence as a control, in which the RF coil was manually tuned/matched to $^2$H and $^{17}$O resonant frequencies, respectively. Then interleaved $^2$H-$^{17}$O MRS data was obtained with a modified single pulse sequence shown in FIG. 12 in which the RF coil was electronically tuned/matched to $^2$H and $^{17}$O resonant frequencies, by controlling the PIN diodes. Total 20 $^2$H-FIDs (nt=1) and 20 $^{17}$O-FIDs (nt=5) were acquired with TR=50 ms and identical for other parameters according to the schematic. All FIDs acquired with original and modified sequences were processed in the same way and the interleaved scans were averaged to compare with the control $^2$H or 17O signals.

Figure 13:
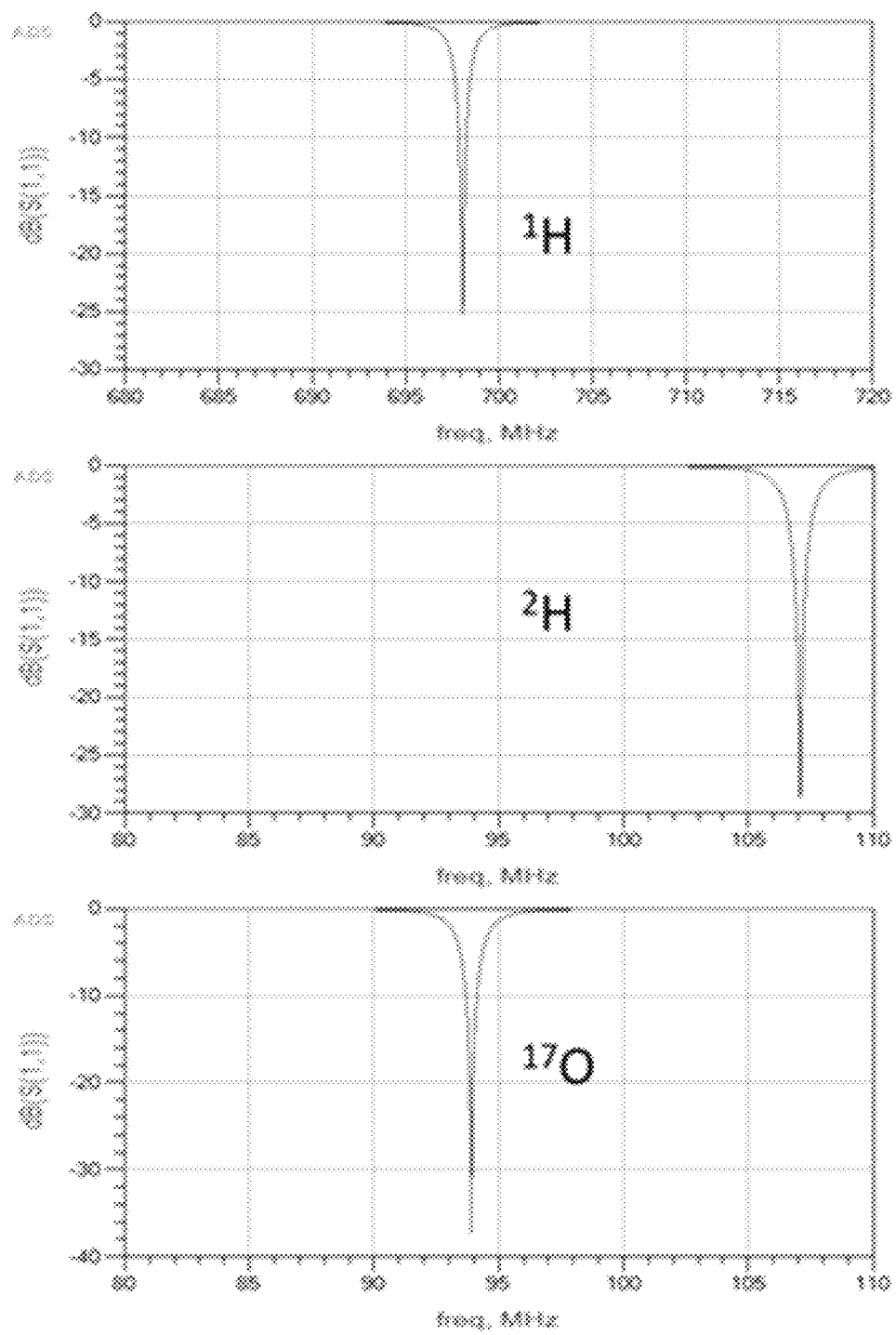
FIG. 13 is a set of correlated graphs of optimal S11 obtained from Keysight's ADS RF simulation at the three targeted resonant frequencies, 698 MHz ($^1$H), 107 MHz ($^2$H), and 94 MHz ($^{17}$O) for MRS, MRSI and MRI applications at 16.4T.
Figure 14:
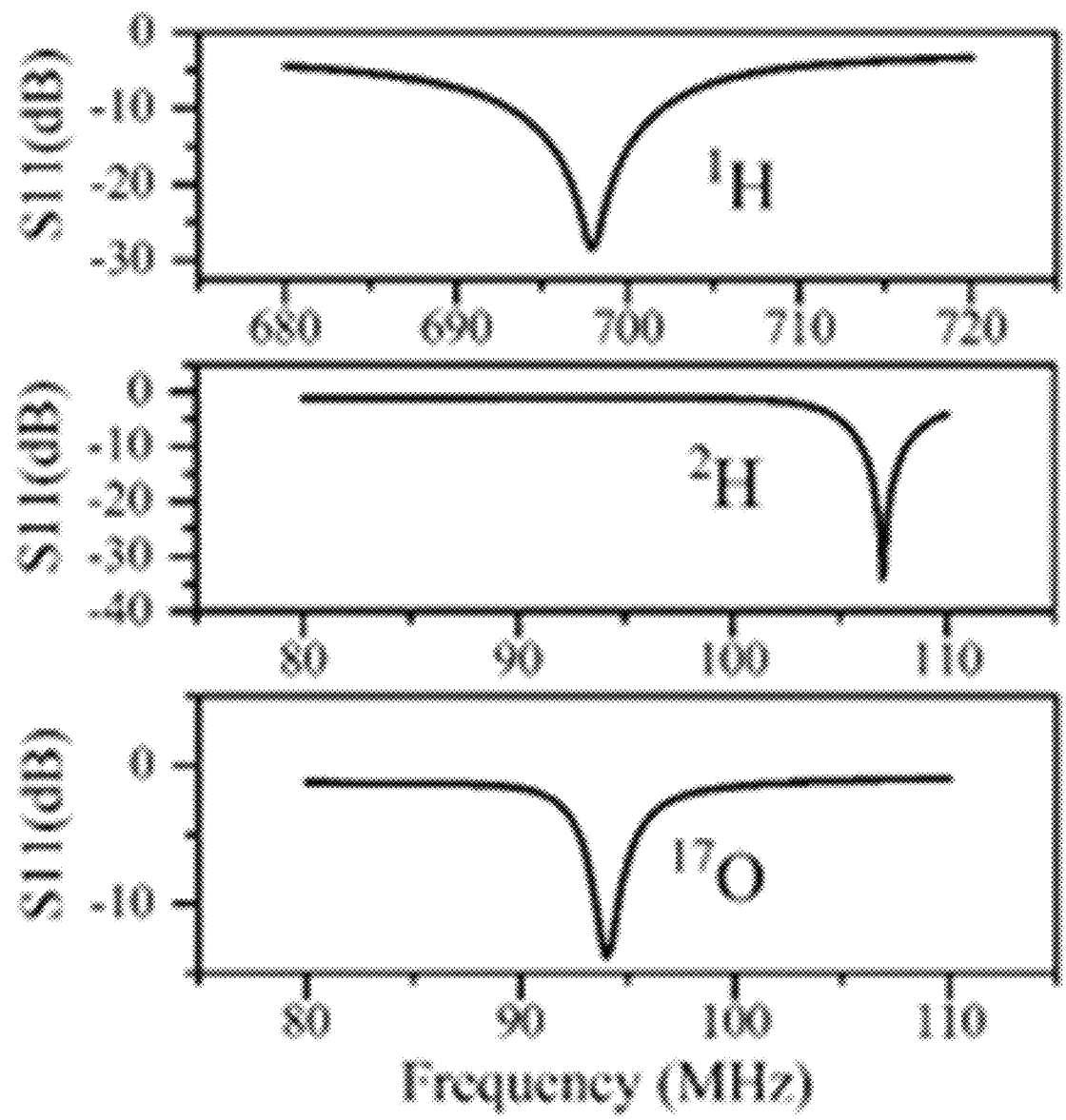
FIG. 14 is a set of correlated graphs showing S11 parameters measured using the Network Analyzer with the new coil (FIG. 11) tuned to three targeted resonant frequencies, 698 MHz ($^1$H), 107 MHz ($^2$H), and 94 MHz ($^{17}$O) at 16.4T.

FIG. 13 provides a set of correlated graphs that shows the simulated reflection coefficients at $^1$H, $^2$H, and $^{17}$O frequencies (at 16.4T) obtained from Keysight's ADS RF simulation software, indicating great performance of the new coil design without loading. FIG. 14 is another set of correlated graphs that shows the actual S11 measurement results of a prototype coil with loading, which was built with optimal components determined in the simulation, indicating a better S11 for $^1$H, similar S11 for $^2$H, and slightly worse S11 for $^{17}$O as compared to the simulation, caused by the loading effect of a large water phantom.

Figure 15A:
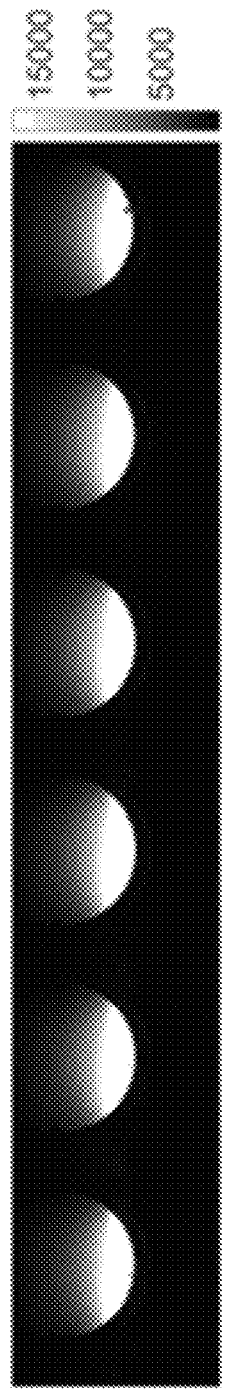
FIG. 15A is a set of $^1$H axial images acquired with 2D GEMS image pulse sequence using the new coil (FIG. 11).
Figure 15B:
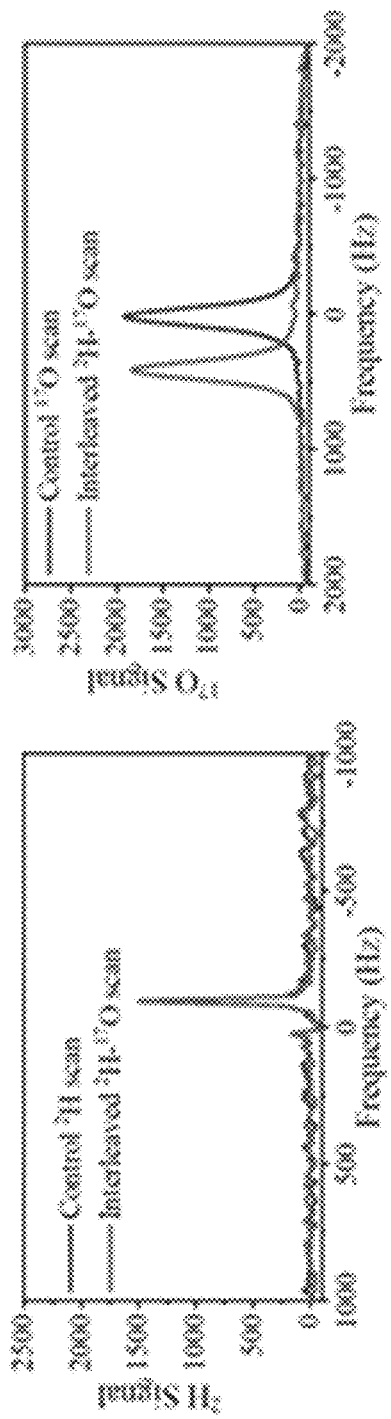
FIG. 15B is a set of correlated graphs of $^2$H signal of control scan and that of interleaved $^2$H-$^{17}$O scans (number of acquisition: nt=20) and $^{17}$O signal of control scan and that of interleaved $^2$H-$^{17}$O scans (nt=100) acquired using the same RF coil of FIG. 11.
Figure 15C:
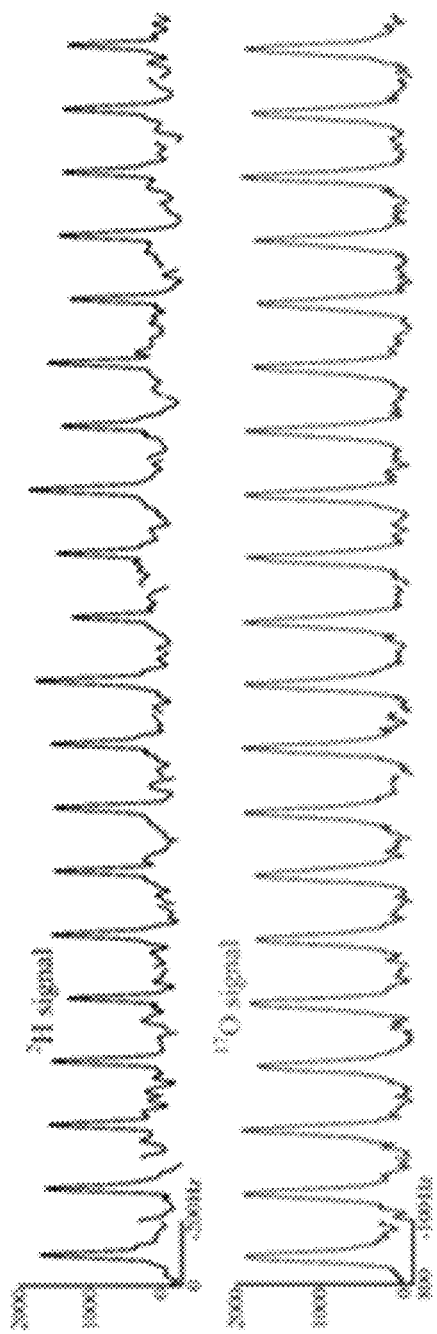
FIG. 15C is a set of correlated graphs of 20 deuterium-2 ($^2$H) spectra from interleaved $^2$H-$^{17}$O scans (nt=1, repeated 20 times) and 20 oxygen-17 ($^{17}$O) spectra from interleaved $^2$H-$^{17}$O scans (nt=5, repeated 20 times) acquired using the same RF coil of FIG. 11.

The phantom test results are summarized in FIGS. 15A-15C. High-quality proton imaging are shown in FIG. 15A.

FIG. 15B is a set of correlated graphs that shows averaged $^2$H and $^{17}$O signals from the interleaved $^2$H-$^{17}$O scan, which matches well with the $^2$H and $^{17}$O signals acquired independently from the control experiments. The averaged interleaved $^{17}$O signal had a ~400 Hz shift from the control signal, which was due to the inaccurate transmitter-frequency setting in the sequence. The slight difference in the signal height was likely caused by this frequency offset. This can be readily corrected. Further, FIG. 15C is a graph that shows arrayed $^2$H and $^{17}$O spectra from interleaved scans and acquired at different time points. The top panel is the deuterium spectra while the bottom panel shows the $^{17}$O spectra.

The results suggest that the same coil can be used to obtain not only the high-fidelity $^1$H anatomic information but also interleaved dynamic measurements of both $^2$H and $^{17}$O signals; thus, has great potential for efficient interleaved metabolic imaging of multiple critical metabolic measures, for instance, cerebral metabolic rate of glucose and TCA cycle rate using the dynamic $^2$H signal and cerebral metabolic rate of oxygen and blood flow using the dynamic $^{17}$O signal as described in Zhu, X. H., Lu M, Chen W., Quantitative imaging of brain energy metabolisms and neuroenergetics using in vivo X-nuclear $^2$H, $^{17}$O and $^{31}$P MRS at ultra-high field. J Magn Reson, 2018; 292:155-170.

Further Design Variation

As described above and illustrated in FIG. 2B, a manual retune/rematching is needed for high or low frequency operation of the circuit of FIG. 2B. However, it is contemplated that switches may be used to electronically switch the operational frequencies. Thus, retuning/rematching can be foregone. In one non-limiting example, FIG. 11 provides an example circuit that includes PIN diodes $C_4$ and $C_3$ that operate as electronic switches to automatically adjust the operation frequency of the circuit.

Figure 16B:
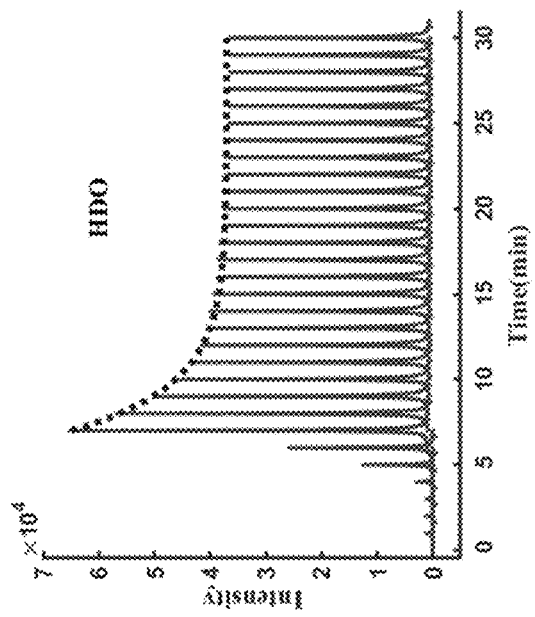
FIG. 16B is a graph of oxygen-17 water (H$_2$$^{17}$O) signal decay plot in rodent brain after an injection of the mixed HDO and H$_2$$^{17}$O water with enriched isotopes acquired with the measurement of FIG. 16A using the same RF coil of FIG. 11 and interleaved RF pulse sequence of FIG. 12.
Figure 16A:
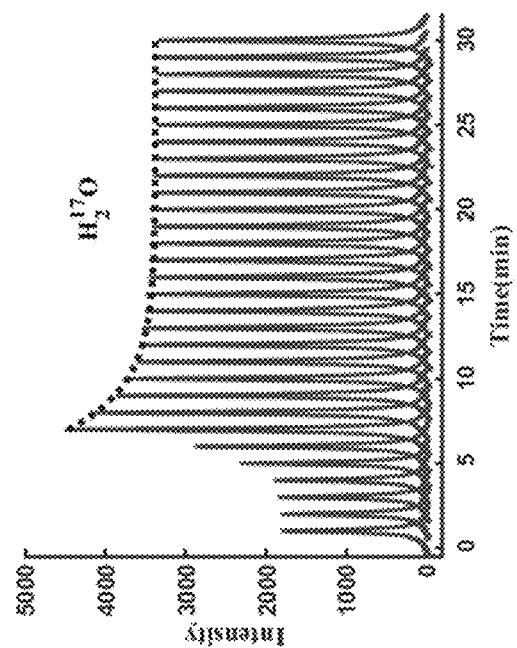
FIG. 16A is a graph of the deuterated water (HDO) signal decay plot in rodent brain after an injection of the mixed HDO and H$_2$$^{17}$O water with enriched isotopes acquired using the same RF coil of FIG. 11 and interleaved pulse sequence of FIG. 12.

Referring to FIGS. 16A and 16B, the results of an in-vivo rat brain study using an IV injection of dual-isotope ($^2$H and $^{17}$O) labeled water at 16.4T are shown. As shown in FIG. 16A, the $^2$H HDO signal decay rate in the rat brain was 0.37 min$^{-1}$. As shown in FIG. 16B, the $^{17}$O water signal decay rate was 0.38 min$^{-1}$. Thus, the study showed the (anticipated) consistent rates measured by the $^2$H and $^{17}$O water tracers, reflecting cerebral blood flow (CBF) detected by the above-described coil system at the same time.

Figure 17:
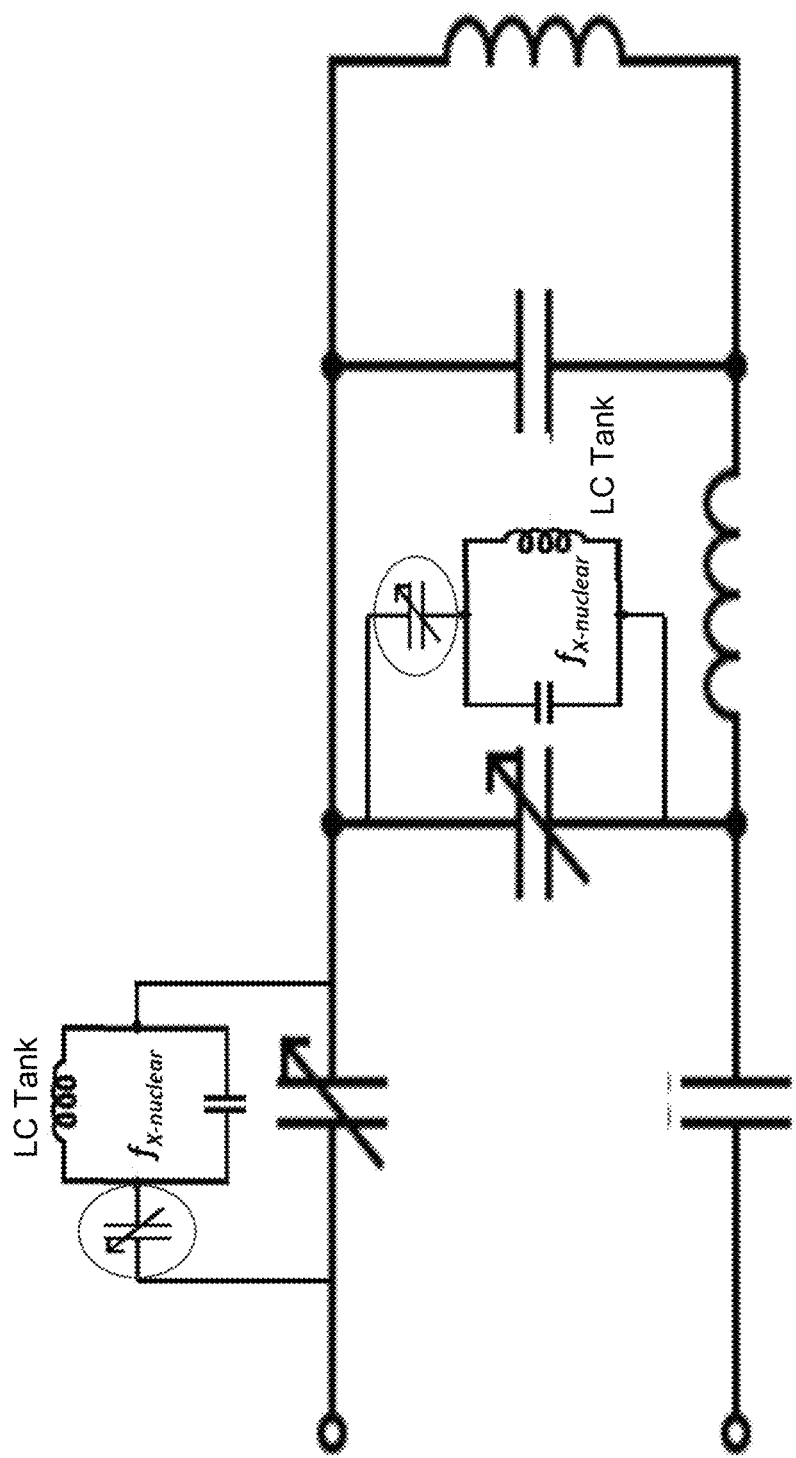
FIG. 17 is a circuit diagram using LC tanks to allow tuning/matching of the same dual-frequency RF coil to two desired (high and low) resonant frequencies without the need of using PIN diodes and DC power controller. This method has been applied to the 8-channel $^1$H-$^2$H dual-frequency head coil array of FIG. 10E.

Referring to FIG. 17, the above-described circuits may be further adapted to use two LC tanks to allow tuning/matching of the same RF coil to two desired (e.g., high and low) operational frequencies without the need for the PIN diodes and the DC power controller as applied in FIG. 11. The self-resonant frequency of the LC tank was tuned to the X-nuclear resonant frequency, thus, acting an open circuit for the low X-nuclear resonant frequency but passing for the high ($^1$H) resonant frequency for adding C3 and C4 capacitances for independently retuning and rematching the coil respectively to the $^1$H resonant frequency, thus, achieving two desired (high and low) resonant frequencies for the same RF coil under optimal tuning/matching conditions (FIG. 17), or verse visa (i.e., set the LC tank self-resonant frequency to $^1$H resonant frequency). This effective approach has been successfully applied to the 7T 8-channel $^1$H-$^2$H dual-frequency human head coil design and construction as shown in FIG. 10E.

The present invention has been described in terms of one or more preferred embodiments, and it should be appreciated that many equivalents, alternatives, variations, and modifications, aside from those expressly stated, are possible and within the scope of the invention.

As used in the claims, the phrase "at least one of A, B, and C" means at least one of A, at least one of B, and/or at least one of C, or any one of A, B, or C or combination of A, B, or C. A, B, and C are elements of a list, and A, B, and C may be anything contained in the Specification.

We claim:

1. A radiofrequency (RF) coil system for performing magnetic resonance imaging (MRI), magnetic resonance spectroscopy (MRS), or magnetic resonance spectroscopy imaging (MRSI) configured to be operated at multiple resonant frequencies, the coil system comprising:
   at least one conductive loop and a capacitor forming an RF resonant antenna;
   a tuning-matching circuit electrically connected to the RF resonant antenna to operate at multiple resonant frequencies across a desired operational range; and
   two conductive legs electrically connecting the tuning-matching circuit to the RF resonant antenna and having a length selected to generate at least two selected resonant frequencies with a selected frequency difference.

2. The coil system of claim 1 wherein the capacitor is connected to the two conductive legs and the RF resonant antenna.

3. The coil system of claim 1 wherein the at least one conductive loop forming the RF resonant antenna includes a plurality of conductive loops forming an arrayed RF coil antenna with multiple resonant frequencies and wherein the RF coil system electrically and magnetically decouples coil channels within the arrayed RF antenna and between the selected frequency difference.

4. The coil system of claim 1 wherein the tuning-matching circuit forms a purely-resistive element.

5. The coil system of claim 1 wherein a quantitative relationship between all capacitances and inductances in the coil system under unloaded conditions, where the induced reactance is zero, is given by:

$$\cfrac{1}{\cfrac{1}{\cfrac{1}{\frac{1}{\omega_0 L_2} - \omega_0 C_4} + \omega_0 L_1} - \omega_0 C_L} - \frac{1}{\omega_0 C_S} - \frac{1}{\omega_0 C_S} = 0;$$

wherein $\omega_0$ represents each of the multiple resonant frequencies of the coil, $C_S$ is a capacitance of a matching capacitor, $C_L$ is a capacitance of a tuning capacitor, $L_1$ is inductance of the two conductive legs, $L_2$ is inductance of the conductive loop, and $C_4$ is a capacitance connected to the two conductive legs and the RF resonant antenna.

6. The coil system of claim 1 wherein the tuning-matching circuit further comprises a resonant frequency switch between two desired resonant frequencies.

7. The coil system of claim 6 wherein the resonant frequency switch includes at least one of a PIN diode switch or a LC tank switch.

8. The coil system of claim 1 wherein the tuning-matching circuit further comprises two LC tanks configured for independent tuning and matching of the RF coil at two desired resonant frequencies at the same time.

9. The coil system of claim 1 wherein the at least one conductive loop forms two coil loops that partially overlap to create a decoupled quadrature coil array.

10. A method for designing a RF coil system for performing magnetic resonance imaging (MRI), magnetic resonance spectroscopy (MRS) or magnetic resonance spectroscopy imaging (MRSI) operated at multiple resonant frequencies, the method comprising:
- selecting at least one conductive loop and at least one capacitor to form a radio frequency (RF) resonant antenna;
- configuring a tuning-matching circuit electrically coupled to the RF resonant antenna to generate multiple resonant frequencies across a desired operational range;
- electrically connecting at least two legs between the tuning-matching circuit and the at least one RF resonant antenna; and
- selecting components of the tuning-matching circuit and parameters of the conductive loop and the at least two legs to have a quantitative relationship between all capacitances and inductances under unloaded conditions, where the induced reactance is zero, using:

$$\frac{1}{\frac{1}{\frac{1}{\frac{1}{\omega_0 L_2} - \omega_0 C_4} + \omega_0 L_1} - \omega_0 C_L} - \frac{1}{\omega_0 C_5} - \frac{1}{\omega_0 C_S} = 0;$$

wherein $\omega_0$ represents each of the multiple resonant frequencies of the coil, $C_S$ is a capacitance of a matching capacitor, $C_L$ is a capacitance of a tuning capacitor, $L_1$ is inductance of the two legs, $L_2$ is inductance of the conductive loop, and $C_4$ is a capacitance connected to the two legs and the RF resonant antenna.

11. The method of claim 10 wherein selecting the at least one conductive loop includes selecting a plurality of conductive loops forming an arrayed RF coil antenna with multiple resonant frequencies and electrically and magnetically decoupling coil channels within the arrayed RF antenna and between two resonant frequencies.

12. The method of claim 11 wherein magnetically decoupling coil channels within the arrayed RF antenna and between the two resonant frequencies includes configuring the at least one conductive loop to form a plurality of overlapped coil structures.

13. The method of claim 10 further comprising forming an inductive-capacitive (LC) loop between the tuning-matching circuit and the RF resonant antenna.

14. The method of claim 10 further comprising forming the tuning-matching circuit as a purely-resistive element.

15. The method of claim 10 further comprising forming a frequency switch in the tuning-matching circuit to switch between two desired resonant frequencies.

16. The method of claim 15 further comprising including at least one of a PIN diode switch or a LC tank switch in the frequency switch.

17. The method of claim 10 further comprising forming two LC tanks in the tuning-matching circuit to configure the RF coil for independent tuning and matching at two desired resonant frequencies at the same time.

18. The method of claim 10 further comprising forming a decoupled dual frequency quadrature coil array using two dual frequency coil loops that partially overlap each other for achieving high decoupling efficiency.

19. The method of claim 18 further comprising more dual frequency coil loops configured to generate decoupled dual frequency coil array with a desired number of coil channels.

* * * * *

UNITED STATES PATENT AND TRADEMARK OFFICE
CERTIFICATE OF CORRECTION

PATENT NO. : 11,883,148 B2
APPLICATION NO. : 17/872793
DATED : January 30, 2024
INVENTOR(S) : Wei Chen et al.

It is certified that error appears in the above-identified patent and that said Letters Patent is hereby corrected as shown below:

In the Specification

Column 3, Line 20, "X/4" should be --$\lambda/4$--.

Column 3, Line 51, "Rutledge 0" should be --Rutledge O--.

Column 5, Line 1, "Li" should be --$L_1$--.

Column 5, Line 41, "1 pF$\leq C_L \leq$23" should be --1 pF$\geq C_L \leq$23--.

Column 5, Line 46, "1 pF$\leq C_L \leq$23" should be --1 pF$\geq C_L \leq$23--.

Column 5, Line 47, "1 pF$\leq C_L \leq$23" should be --1 pF$\geq C_L \leq$23--.

Column 5, Line 52, "1 pF$\leq C_L \leq$23" should be --1 pF$\geq C_L \leq$23--.

Column 5, Line 53, "1 pF$\leq C_L \leq$23" should be --1 pF$\geq C_L \leq$23--.

Column 5, Line 59, "170" should be --$^{17}$O--.

Column 11, Line 7, "(o)" should be --($\omega_0$)--.

Column 13, TABLE 1, Line 4, "Iloop" should be --$I_{loop}$--.

Column 13, TABLE 1, Line 5, "Ileg" should be --$I_{leg}$--.

Column 13, TABLE 1, Line 7, "Iloop" should be --$I_{loop}$--.

Column 13, TABLE 1, Line 14, "Iloop" should be --$I_{loop}$--.

Signed and Sealed this
Ninth Day of April, 2024

*Katherine Kelly Vidal*
Katherine Kelly Vidal
*Director of the United States Patent and Trademark Office*

Column 13, TABLE 1, Line 15, "Ileg" should be --$I_{leg}$--.

Column 13, TABLE 1, Line 18, "Iloop" should be --$I_{loop}$--.

Column 13, TABLE 1, Line 19, "Ileg" should be --$I_{leg}$--.

Column 13, TABLE 1, Line 24, "Iloop" should be --$I_{loop}$--.

Column 13, TABLE 1, Line 25, "Ileg" should be --$I_{leg}$--.

Column 14, Line 36, "field. journal" should be --field. Journal--.

Column 20, Line 30, "low-y" should be --low-$\gamma$--.

Column 20, Line 34, "low-y" should be --low-$\gamma$--.

Column 21, Line 15, "at 7T" should be --at $\geq$ 7T--.

Column 22, Line 54, "170" should be --$^{17}O$--.